(12) United States Patent
Sugie et al.

(10) Patent No.: US 11,302,439 B2
(45) Date of Patent: Apr. 12, 2022

(54) MEDICAL IMAGE PROCESSING APPARATUS, MEDICAL IMAGE PROCESSING METHOD, AND COMPUTING DEVICE

(71) Applicant: Sony Corporation, Tokyo (JP)

(72) Inventors: Yuki Sugie, Kanagawa (JP); Daisuke Tsuru, Chiba (JP); Tomoyuki Hirayama, Kanagawa (JP); Kenta Yamaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 60 days.

(21) Appl. No.: 16/624,926

(22) PCT Filed: Jun. 13, 2018

(86) PCT No.: PCT/JP2018/022524
§ 371 (c)(1),
(2) Date: Dec. 20, 2019

(87) PCT Pub. No.: WO2019/003911
PCT Pub. Date: Jan. 3, 2019

(65) Prior Publication Data
US 2020/0135330 A1 Apr. 30, 2020

(30) Foreign Application Priority Data

Jun. 27, 2017 (JP) .............................. JP2017-125245
Nov. 7, 2017 (JP) .............................. JP2017-215066

(51) Int. Cl.
*G06K 9/00* (2006.01)
*G16H 30/40* (2018.01)
(Continued)

(52) U.S. Cl.
CPC ........... *G16H 30/40* (2018.01); *G06K 9/3233* (2013.01); *G06T 1/20* (2013.01); *G06T 7/0012* (2013.01); *G16H 40/63* (2018.01)

(58) Field of Classification Search
CPC ........ G16H 30/40; G16H 40/63; G16H 50/20; G16H 20/40; G06K 9/3233; G06K 2209/05; G06K 9/209; G06T 1/20; G06T 7/0012
See application file for complete search history.

(56) References Cited

U.S. PATENT DOCUMENTS 8,117,549 B2 * 2/2012 Reiner ............... G06Q 10/0633
715/751
2005/0078861 A1 * 4/2005 Usikov ................. G06T 11/006
382/131
(Continued)

FOREIGN PATENT DOCUMENTS

EP 2989987 A1 3/2016
WO WO2016035094 * 3/2016 ............... A61B 6/00

OTHER PUBLICATIONS

Zbigniew et al, ("FPGA implementations of a parallel associative processor with multi-comparand multi-search operations", 2008 International Symposium on Parallel and Distributed Computing, pp. 444-448) (Year: 2008).*

(Continued)

*Primary Examiner* — Amara Abdi
(74) *Attorney, Agent, or Firm* — Xsensus LLP

(57) ABSTRACT

A medical image processing apparatus for allocating at least two medical imaging processes to a plurality of assignable processing resources is provided. The plurality of assignable processing resources is allocated by the medical image processing apparatus based on resource information of the plurality of assignable processing resources. The medical image processing apparatus includes circuitry configured to
(Continued)

acquire medical image processing content, from medical equipment, to be processed according to the at least two medical imaging processes prior to display on a display device connected to a surgical operating room network. The circuitry is configured to acquire the resource information of the plurality of assignable processing resources, and allocate each of the at least two medical imaging processes to a different one of the plurality of assignable processing resources based on the resource information of the plurality processing resources and the medical image processing content.

19 Claims, 18 Drawing Sheets

(51) Int. Cl.
    *G16H 40/63*     (2018.01)
    *G06K 9/32*     (2006.01)
    *G06T 1/20*     (2006.01)
    *G06T 7/00*     (2017.01)

(56) References Cited

U.S. PATENT DOCUMENTS

| | | | |
|---|---|---|---|
| 2005/0113680 A1* | 5/2005 | Ikeda | A61B 6/504 600/425 |
| 2006/0184475 A1* | 8/2006 | Krishnan | G16H 10/60 706/20 |
| 2007/0014454 A1* | 1/2007 | Sawyer | A61N 5/1049 382/128 |
| 2008/0229318 A1* | 9/2008 | Franke | G06F 9/505 718/104 |
| 2010/0239065 A1* | 9/2010 | Tsubota | A61B 6/00 378/62 |
| 2011/0040169 A1 | 2/2011 | Kamen et al. | |
| 2011/0200227 A1* | 8/2011 | Bogoni | G06T 7/0016 382/103 |
| 2012/0221728 A1 | 8/2012 | Dubbels et al. | |
| 2012/0249416 A1 | 10/2012 | Maciocci et al. | |
| 2013/0089249 A1* | 4/2013 | Mueller | G06K 9/0014 382/128 |
| 2013/0253325 A1 | 9/2013 | Call et al. | |
| 2014/0016005 A1* | 1/2014 | Kishima | H04N 5/3675 348/246 |
| 2014/0253573 A1* | 9/2014 | Rettig | G06T 1/20 345/531 |
| 2015/0002394 A1* | 1/2015 | Cho | G02B 27/0093 345/156 |
| 2016/0136458 A1* | 5/2016 | Taguchi | A61B 6/5223 382/132 |
| 2016/0142645 A1* | 5/2016 | Shionoya | H04N 5/265 348/218.1 |
| 2017/0083762 A1* | 3/2017 | Segalovitz | G06K 9/00463 |
| 2017/0300620 A1* | 10/2017 | Rahme | G16H 15/00 |

OTHER PUBLICATIONS

International Search Report and Written Opinion dated Aug. 29, 2018 for PCT/JP2018/022524 filed on Jun. 13, 2018, 12 pages.

* cited by examiner

| Machine name | Reservation status | Operation status | Rate | Available time | Selectable processing |
|---|---|---|---|---|---|
| Hospital CCU | | busy | 0 Yen/H | 3H after 2H | Image-quality enhancement |
| Hospital server | | busy | 0 Yen/H | 2H after 4H | Image-quality enhancement, Detection of bleeding |
| cloud1 | Primary reservation | available | 5,000 Yen/H | 5H | Image-quality enhancement, Detection of bleeding, Pathological analysis |
| cloud2 | Secondary reservation | available | 5,000 Yen/H | 12H | Image-quality enhancement, Detection of bleeding, Pathological analysis |
| cloud3 | | busy | 8,000 Yen/H | 12H after 8H | Image-quality enhancement, Detection of bleeding, Pathological analysis, Remote assistance |

FIG.18

MEDICAL IMAGE PROCESSING APPARATUS, MEDICAL IMAGE PROCESSING METHOD, AND COMPUTING DEVICE

CROSS-REFERENCE TO RELATED APPLICATIONS

This application is based on PCT filing PCT/JP2018/022524, filed Jun. 13, 2018, which claims the benefit of Japanese Priority Patent Application JP 2017-125245, filed Jun. 27, 2017, and Japanese Priority Patent Application JP 2017-215066, filed Nov. 7, 2017, the entire contents of each are incorporated herein by reference.

TECHNICAL FIELD

The present disclosure relates to an information processing apparatus and method, and an information processing system, and particularly to an information processing apparatus and method, and an information processing system that are capable of improving the utilization efficiency of resources.

BACKGROUND ART

In the past, medical therapeutic equipment such as an endoscope system has been designed to have redundancy by including a plurality of signal processing devices, e.g., devices for normal use and devices for emergency use, such that in case of malfunction of the signal processing devices for normal use, the rest of the signal processing devices for emergency use perform processing for the purpose of avoiding interruption of treatment (see, for example, Patent Literature 1).

CITATION LIST

Patent Literature

PTL 1: WO 2015/163171

SUMMARY OF INVENTION

Technical Problem

However, in this method, the signal processing devices for emergency use have generally been allowed to perform only the same processing as that of the signal processing devices for normal use, and thus the image processing function thereof has been limited to processing content available for the signal processing devices for normal use. Therefore, in a case where image-quality enhancement processing that improves the procedure efficiency of a surgeon exceeds the processing content available for the signal processing devices for normal use, there has been a possibility that the image-quality enhancement processing is difficult to achieve.

The present disclosure has been made in view of the circumstances as described above and aims at improving the utilization efficiency of resources and also achieving processing with higher performance.

Solution to Problem

In one embodiment, there provided a medical image processing apparatus for allocating at least two medical imaging processes to a plurality of assignable processing resources. The plurality of assignable processing resources is allocated by the medical image processing apparatus based on resource information of the plurality of assignable processing resources. The medical image processing apparatus includes circuitry configured to acquire medical image processing content, from medical equipment, to be processed according to the at least two medical imaging processes prior to display on a display device connected to a surgical operating room network. The circuitry is configured to acquire the resource information of the plurality of assignable processing resources. Further, the circuitry is configured to allocate each of the at least two medical imaging processes to a different one of the plurality of assignable processing resources based on the resource information of the plurality processing resources and the medical image processing content.

In one embodiment, there provided a medical image processing method, executed in a medical image processing apparatus, for allocating at least two medical imaging processes to a plurality of assignable processing resources. The plurality of assignable processing resources is allocated by the medical image processing apparatus based on resource information of the plurality of assignable processing resources. The medical image processing method includes acquiring with the circuitry medical image processing content, from medical equipment, to be processed according to the at least two medical imaging processes prior to display on a display device connected to a surgical operating room network. The method includes acquiring the resource information of the plurality of assignable processing resources. The method further includes allocating with the circuitry each of the at least two medical imaging processes to a different one of the plurality of assignable processing resources based on the resource information of the plurality of assignable processing resources and the medical image processing content.

In one embodiment, there provided a computing device including a display and circuitry. The circuitry is configured to present on the display first icons representing medical image processes to be performed on medical image content, and second icons representing at least one type of assignable processing resource. The second icons are displayed on the display in association with the first icons to indicate which of the assignable processing resources have been assigned to perform a particular one of the medical image processes. Further, allocation of the assignable processing resources are assignable from a menu of user-selectable resource information that lists the assignable processing resources that are available to be assigned to the medical image processes represented by the first icons.

In one embodiment, there provided a same computing device in which the circuitry is configured to display user-selectable control features that include at least one of a frame size and/or shape of a region of interest, a resource allocation indication, a usage fee, an occupancy allocation, and an operation time of using a fee-for-use cloud processing resource.

In one embodiment, there provided a same computing device with cloud computing resources being selectable as an external processing resource.

Advantageous Effects of Invention

According to the present disclosure, the utilization efficiency of resources at information processing can be improved.

BRIEF DESCRIPTION OF DRAWINGS

FIG. 18 is a diagram for describing an example of a user interface.

DESCRIPTION OF EMBODIMENTS

Hereinafter, modes for carrying out the present disclosure (hereinafter referred to as embodiments) will be described. It should be noted that description will be given in the following order.

1. Image Processing Performance of Endoscope System
2. First Embodiment (endoscopic surgery system, using plurality of resources within CCU)
3. Second Embodiment (CCU system, using another CCU resource)
4. Third Embodiment (CCU system, using plurality of CCU resources)
5. Fourth Embodiment (CCU system, using cloud computing)
6. Others

1. Image Processing Performance of Endoscope System

In the past, medical therapeutic equipment (or medical equipment) such as an endoscope system has been designed to have redundancy by including a plurality of signal processing devices, e.g., devices for normal use and devices for emergency use, such that in case of malfunction of the signal processing devices for normal use, the rest of the signal processing devices for emergency use perform processing for the purpose of avoiding interruption of treatment.

In such a system, the signal processing devices for emergency use have generally been allowed to perform only the same processing as that of the signal processing devices for normal use. As a result, the image processing performance thereof has been limited to processing content available for the signal processing devices for normal use. Therefore, for example, in a case where image-quality enhancement processing that improves the procedure efficiency of a surgeon exceeds the processing content available for the signal processing devices for normal use, the image-quality enhancement processing has been difficult to achieve.

2. First Embodiment

Distribution of Processing

In this regard, processing regarding instant output of medical data is configured to be adaptively distributed to a plurality of arithmetic processing sections. This configuration can improve the utilization efficiency of resources. This allows achievement of higher-performance processing than that of each arithmetic processing section. For example, a high-quality endoscopic image that is difficult to achieve by a single arithmetic processing section can be provided to the surgeon, and surgery procedure can be improved.

Further, by use of the plurality of arithmetic processing sections, the processing can be performed at higher speed than in a case where a single arithmetic processing section is used. Furthermore, arithmetic performance and the like that are expected for each of the arithmetic processing sections can be reduced, and thus increase in costs can be suppressed. It should be noted that high-performance processing is not limited to the image-quality enhancement processing and may be surgical assistance processing such as highlighting a lesion site and displaying a cut part of the lesion site on an image in a superimposed manner.

Endoscopic Surgery System

Figure 1:
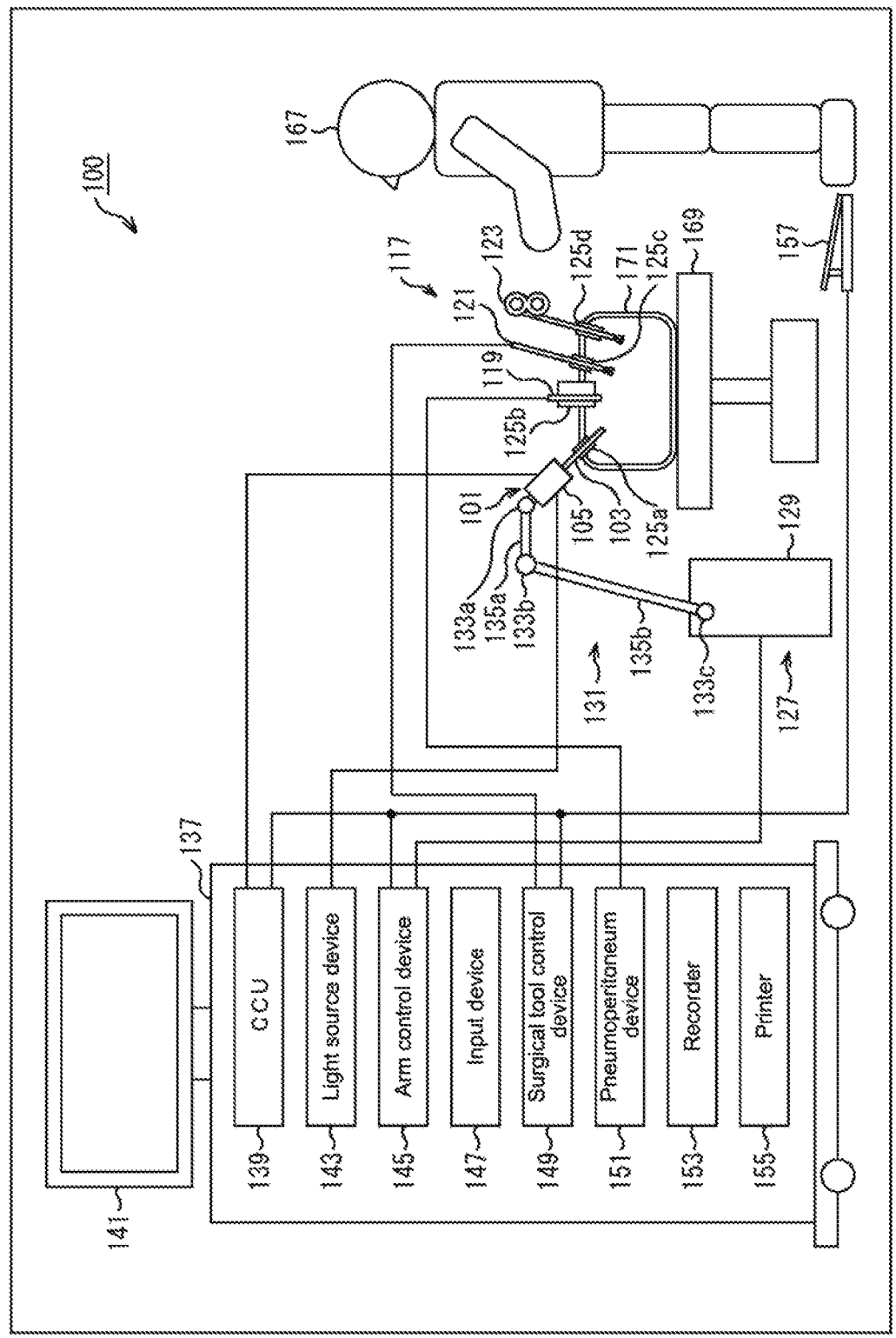
FIG. 1 is a diagram of a schematic configuration example of an endoscopic surgery system.

FIG. 1 is a diagram illustrating an example of a schematic configuration of an endoscopic surgery system 100, to which the technology according to the present disclosure may be applied. FIG. 1 illustrates that a surgeon (doctor) 167 performs surgery on a patient 171 on a patient bed 169 by using the endoscopic surgery system 100. As illustrated in the figure, the endoscopic surgery system 100 includes an endoscope 101, other surgical instruments 117, a support arm device 127 that supports the endoscope 101, and a cart 137 including various kinds of built-in endoscopic surgical devices.

In endoscopic surgery, instead of laparotomy by incising the abdominal wall, the abdominal wall is punctured by a plurality of tubular puncture instruments called trocars 125a to 125d. A lens tube 103 of the endoscope 101 and other surgical instruments 117 are inserted into the body cavity of the patient 171 through the trocars 125a to 125d. In the illustrated example, a pneumoperitoneum tube 119, an energy surgical tool 121, and a forceps 123 are inserted, as other surgical instruments 117, into the body cavity of the patient 171. Further, the energy surgical tool 121 is a surgical tool that performs cutting and peeling of tissues, sealing of a blood vessel, or the like by a high-frequency current or ultrasonic vibration. It should be noted that the surgical instruments 117 illustrated in the figure are merely exemplary. For the surgical instruments 117, for example, various surgical instruments generally used in endoscopic surgery, such as tweezers and retractors, may be used.

An image of a surgery site within the body cavity of the patient 171, which is captured by the endoscope 101, is displayed on a display device 141. The surgeon 167 performs the procedure, e.g., removal of an affected part, by using the energy surgical tool 121 or the forceps 123 while watching in real time the image of the surgery site that is displayed on the display device 141. It should be noted that the pneumoperitoneum tube 119, the energy surgical tool 121, and the forceps 123 are supported by the surgeon 167, an assistant, or the like during the surgery, though not illustrated in the figure.

Support Arm Device

The support arm device 127 includes an arm portion 131 that extends from a base portion 129. In the illustrated example, the arm portion 131 includes joints 133a, 133b, and 133c, and links 135a and 135b, and is driven by the control of an arm control device 145. The arm portion 131 supports the endoscope 101 and controls the position and posture of the endoscope 101. This may allow the endoscope 101 to be fixed at a stable position.

Endoscope

The endoscope 101 includes the lens tube 103 and a camera head 105, part of the lens tube 103 from the tip having a predetermined length being inserted in the body cavity of the patient 171, the camera head 105 being connected to the base of the lens tube 103. The figure illustrates the endoscope 101 including the rigid lens tube 103, i.e., a so-called rigid endoscope, for example. Alternatively, the endoscope 101 may be a so-called flexible endoscope including a flexible lens tube 103.

The lens tube 103 has an opening at the tip, an objective lens being fitted in the opening. A light source device 143 is connected to the endoscope 101. The light source device 143 generates light, a light guide extending in the lens tube 103 guides the light to the tip of the lens tube, the light passes through the objective lens, and an object of observation in the body cavity of the patient 171 is irradiated with the light. It should be noted that the endoscope 101 may be a direct-viewing endoscope, an oblique-viewing endoscope, or a side-viewing endoscope.

The camera head 105 includes an optical system and an image sensor inside. Reflected light (observation light) from the object of observation is condensed on the image sensor by the optical system. The image sensor photoelectrically converts the observation light to thereby generate an electric signal corresponding to the observation light, i.e., an image signal corresponding to an observation image. The image signal, as raw data, is transmitted to a camera control unit (CCU) 139. It should be noted that the camera head 105 is provided with a function of adjusting a magnifying power and a focal length by appropriately driving the optical system.

It should be noted that, in order to correspond to stereoscopy (3D (dimensional) display) or the like, the camera head 105 may include a plurality of image sensors. In this case, the lens tube 103 includes a plurality of series of relay optical systems in order to guide the observation light to each of the image sensors.

Various Devices Mounted on Cart

The CCU 139 includes a central processing unit (CPU), a graphics processing unit (GPU), or the like, and centrally controls the operation of the endoscope 101 and the display device 141. The display device can be connected via a surgical operating room network. For example, the CCU 139 causes the display device 141 to instantly (in real time) display a captured image or the like captured by the endoscope 101. Specifically, the CCU 139 receives the image signal from the camera head 105, and immediately performs various types of image processing, e.g., development processing (demosaicing processing), on the image signal, to display an image based on the image signal. The CCU 139 provides the image signal subjected to the image processing to the display device 141. Further, the CCU 139 transmits a control signal to the camera head 105 and controls its driving. The control signal may include information regarding imaging conditions such as a magnifying power and a focal length.

Controlled by the CCU 139, the display device 141 displays an image based on the image signal subjected to the image processing by the CCU 139. In a case where the endoscope 101 corresponds to imaging in high resolution, e.g., 4K (the number of horizontal pixels 3840 by the number of vertical pixels 2160) or 8K (the number of horizontal pixels 7680 by the number of vertical pixels 4320), and/or corresponds to 3D display, one capable of high-resolution display and/or one capable of 3D display may be used as the display device 141 so as to respectively correspond thereto. In a case where the endoscope 101 corresponds to imaging in high resolution such as 4K or 8K, use of a display device 141 having the size of 55 inches or more provides a greater sense of immersion. Alternatively, depending on purposes, a plurality of display devices 141 having different resolutions and sizes may be provided.

The light source device 143 includes a light source such as a light emitting diode (LED), for example, and supplies light to the endoscope 101, a surgery site being irradiated with the light when its image is captured.

The arm control device 145 includes a processor such as a CPU and operates according to a predetermined program to control the driving of the arm portion 131 of the support arm device 127 according to a predetermined control method.

An input device 147 is an input interface for the endoscopic surgery system 100. A user may input various kinds of information and instructions in the endoscopic surgery system 100 via the input device 147. For example, a user inputs various types of information regarding surgery, such as physical information of a patient and the procedure of the surgery, via the input device 147. Further, for example, a user inputs, via the input device 147, instructions to drive the arm portion 131, instructions to change imaging conditions (kind of irradiation light, magnifying power, focal length, and the like) of the endoscope 101, instructions to drive the energy surgical tool 121, and other instructions.

The type of the input device 147 is not limited. The input device 147 may be various well-known input devices. For the input device 147, for example, a mouse, a keyboard, a touch panel, a switch, a foot switch 157, and/or a lever may be applied. In a case where a touch panel is used as the input device 147, the touch panel may be provided on the display screen of the display device 141.

Alternatively, the input device 147 is a device wearable (or wearable computer) by a user, such as a glasses-type wearable device or a head mounted display (HMD), and receives various inputs depending on gestures and the line of sight of the user, which are detected by those devices. Further, the input device 147 includes a camera that can detect a motion of a user, and receives various inputs depending on gestures and the line of sight of the user, which are detected from a video captured by the camera. Furthermore, the input device 147 includes a microphone that can collect voice of a user, and receives various inputs through the voice via the microphone. In such a manner, the input device 147 is configured to be capable of inputting various types of information in a contactless manner, so that a user (e.g., surgeon 167) particularly belonging to a clean area can operate devices belonging to an unclean area in a contactless manner. Further, the user can operate the devices without releasing a surgical instrument held in hand, and the convenience of the user is improved.

A surgical tool control device 149 controls the driving of the energy surgical tool 121 that cauterizes a tissue, incises a tissue, seals a blood vessel, or the like. A pneumoperitoneum device 151 feeds gas into the body cavity of the patient 171 via the pneumoperitoneum tube 119 in order to swell up the body cavity for the purpose of securing the imaging field of the endoscope 101 and securing the workspace for a surgeon. A recorder 153 is a device capable of recording various kinds of surgical information. A printer 155 is a device capable of printing the various kinds of surgical information in various kinds of formats such as a text, an image, and a graph.

Hereinafter, a particularly characteristic configuration of the endoscopic surgery system 100 will be described in further detail.

Support Arm Device

The support arm device 127 includes the base portion 129 as a base, and the arm portion 131 that extends from the base portion 129. In the illustrated example, the arm portion 131 includes the plurality of joints 133a, 133b, and 133c, and the plurality of links 135a and 135b coupled to each other by the joint 133b. FIG. 1 illustrates a simplified configuration of the arm portion 131 for simplicity. Actually, in order to provide the arm portion 131 with a desired degree of freedom, the shape, the number, and the arrangement of the joints 133a to 133c and the links 135a and 135b, and the directions of rotation shafts of the joints 133a to 133c and the like may be appropriately set. For example, the arm portion 131 may be suitably configured to have 6 degrees of freedom or more. This allows the endoscope 101 to be freely moved in the movable range of the arm portion 131, and thus the lens tube 103 of the endoscope 101 can be inserted into the body cavity of the patient 171 from a desired direction.

The joints 133a to 133c includes actuators and are each configured to be rotatable about a predetermined rotation shaft by the driving of the actuators. The arm control device 145 controls the driving of the actuators, and thus a rotational angle of each of the joints 133a to 133c is controlled and the driving of the arm portion 131 is controlled. This can achieve control of the position and the posture of the endoscope 101. In this case, the arm control device 145 can control the driving of the arm portion 131 by various well-known control methods such as force control or position control.

For example, the surgeon 167 may appropriately input an operation via the input device 147 (including the foot switch 157), so that the arm control device 145 appropriately controls the driving of the arm portion 131 according to the input operation to control the position and the posture of the endoscope 101. By this control, the endoscope 101 at the tip of the arm portion 131 can be moved from an arbitrary position to another arbitrary position and fixedly supported at a position after the movement. It should be noted that the arm portion 131 may be operated by a so-called master/slave system. In this case, the arm portion 131 may be remotely operated by a user via the input device 147 installed away from a surgery room.

Further, in a case where the force control is applied, the arm control device 145 may perform so-called power assist control, i.e., receiving external force from a user and driving the actuator of each of the joints 133a to 133c such that the arm portion 131 smoothly moves according to that external force. This allows the user to move the arm portion 131 with a relatively light force when moving the arm portion 131 while touching the arm portion 131 directly. Therefore, it is possible to move the endoscope 101 more intuitively and with a simpler operation and to improve the convenience of the user.

Here, in general, in endoscopic surgery, a doctor called scopist has supported the endoscope 101. To the contrary, use of the support arm device 127 allows the position of the endoscope 101 to be more reliably fixed without human aid. Thus, an image of a surgery site can be stably acquired, and the surgery can be smoothly performed.

It should be noted that the arm control device 145 may not be necessarily provided to the cart 137. Further, the arm control device 145 may not be necessarily one device. For example, the arm control device 145 may be provided to each of the joints 133a to 133c of the arm portion 131 of the support arm device 127. By cooperation of the plurality of arm control devices 145 with one another, the driving of the arm portion 131 may be controlled.

Light Source Apparatus

The light source device 143, which supplies irradiation light to the endoscope 101 when an image of a surgery site is captured, may include an LED, a laser light source, or a white light source including a combination of them, for example. Where the white light source includes a combination of RGB laser light sources, the light source device 143 may adjust the white balance of a captured image since the output intensity and the output timing of each color (each wavelength) may be controlled with a high degree of accuracy. Further, in this case, by irradiating an object of observation with laser light from the respective RGB laser light sources in time-division and by controlling the driving of the image sensor of the camera head 105 in synchronization with the irradiation timings, images respectively corresponding to RGB may be captured in time-division. In accordance with this method, the image sensor without color filters may provide color images.

Further, the driving of the light source device 143 may be controlled to change the intensity of output light at predetermined time intervals. By controlling the driving of the image sensor of the camera head 105 in synchronization with the timings of changing the intensity of the light to thereby obtain images in time-division and by combining the images, high-dynamic-range images without so-called black-clipping and white-clipping may be generated.

Further, the light source device 143 may be configured to be capable of supplying light having a predetermined wavelength band corresponding to special light imaging. An example of the special light imaging is so-called narrow band imaging (NBI), which makes use of the fact that absorption of light by a body tissue depends on the wavelength of light. In the narrow band imaging, a body tissue is irradiated with light having a narrower band than the band of irradiation light (i.e., white light) in the normal imaging, and thereby a high-contrast image of a predetermined tissue such as a blood vessel of a mucous membrane surface is captured. Another possible example of the special light imaging is fluorescence imaging, in which a body tissue is irradiated with excitation light, fluorescence is thereby generated, and a fluorescence image is obtained. In the fluorescence imaging, a body tissue is irradiated with excitation light, and fluorescence from the body tissue is imaged (auto-fluorescence imaging). For another possible example, a reagent such as indocyanine green (ICG) is locally injected into a body tissue and, in addition, the body tissue is irradiated with excitation light corresponding to the fluorescence wavelength of the reagent to thereby obtain a fluorescence image. The light source device 143 may be configured to be capable of supplying narrow band light and/or excitation light corresponding to the special light imaging.

Endoscope

The observation light taken from the tip of the lens tube 103 is guided to the camera head 105 and enters a lens unit. The lens unit of the camera head 105 includes a plurality of lenses including a zoom lens and a focus lens in combination. Optical characteristics of the lens unit are adjusted such that the observation light is condensed on the light-receiving surface of the image sensor. Further, the positions of the zoom lens and the focus lens on the optical axes thereof are configured to be movable for the adjustment of a magnifying power and a focal length of a captured image.

The observation light passes through the lens unit described above and is condensed on the light-receiving surface of the image sensor, and an image signal corresponding to an observation image is generated by photoelectric conversion. The image signal thus generated is provided to a communication section.

This image sensor is, for example, a complementary metal oxide semiconductor (CMOS)-type image sensor, and an image sensor capable of color imaging using a Bayer array is used therefor. It should be noted that, for this image sensor, an image sensor capable of supporting imaging in high resolution of, for example, 4K or more may be used. Since high-resolution images of the surgery site are obtained, the surgeon 167 can grasp the state of that surgery site in more details and can advance the surgery more smoothly.

Further, this image sensor includes a pair of image sensors for obtaining right-eye and left-eye image signals corresponding to 3D display. Thanks to the 3D display, the surgeon 167 is capable of grasping the depth of a biological tissue at a surgery site more accurately. It should be noted that when the image sensor includes multiple image sensors, a plurality of series of lens units may be provided correspondingly to the image sensors, respectively.

Further, the image sensor is not necessarily provided in the camera head 105. For example, the image sensor may be provided immediately after the objective lens in the lens tube 103.

In the camera head 105, the actuator causes the zoom lens and the focus lens of the lens unit to move by a predetermined distance along the optical axis. As a result, the magnifying power and the focus of the captured image may be adjusted appropriately.

Further, the communication section of the camera head 105 includes a communication device for transmitting/receiving various kinds of information to/from the CCU 139. The communication section transmits the image signal obtained from the image sensor, as raw data, to the CCU 139 via a transmission cable. In this case, in order to display the captured image of the surgery site with a low latency, it is desirable to transmit the image signal by optical communication. This is because, in surgery, the surgeon 167 performs surgery while observing the status of the affected part through the captured image, and thus a moving image of the surgery site is expected to be displayed in real time (instantly) to the extent possible for safer and more reliable surgery. When the optical communication is performed, the communication section includes a photoelectric conversion module that converts an electric signal into an optical signal. The image signal is converted into the optical signal by the photoelectric conversion module and then transmitted to the CCU 139 via the transmission cable.

Further, the communication section of the camera head 105 receives a control signal related to driving control of the camera head 105 from the CCU 139. The control signal includes information regarding imaging conditions, which includes information for specifying the frame rate of a captured image, information for specifying the exposure level when capturing an image, information for specifying the magnifying power and the focus of a captured image, and/or the like. The communication section provides the received control signal to a camera head control section. It should be noted that the control signal from the CCU 139 may also be transmitted by the optical communication. In this case, the communication section includes a photoelectric conversion module that converts an electric signal into an optical signal. The control signal is converted into an electric signal by the photoelectric conversion module and then provided to the camera head control section.

It should be noted that the above-mentioned imaging conditions such as the frame rate, the exposure level, the magnifying power, and the focus are automatically set by the CCU 139 on the basis of the acquired image signal. In other words, the endoscope 101 has so-called auto exposure (AE) function, auto focus (AF) function, and auto white balance (AWB) function.

The camera head control section of the camera head 105 controls the driving of the camera head 105 on the basis of the control signal received from the CCU 139 via the communication section. For example, the camera head control section controls the driving of the image sensor on the basis of information for specifying the frame rate of a captured image and/or information for specifying the exposure level when capturing an image. Further, for example, the camera head control section causes the zoom lens and the focus lens of the lens unit to move appropriately on the basis of the information for specifying the magnifying power and the focus of the captured image. The camera head control section may further have a function of storing information for identifying the lens tube 103 and the camera head 105.

It should be noted that the configuration of the lens unit, the image sensor, or the like is disposed in a sealed structure with high air tightness and waterproof property, so that the camera head 105 can be provided with resistance to autoclave sterilization.

Figure 2:
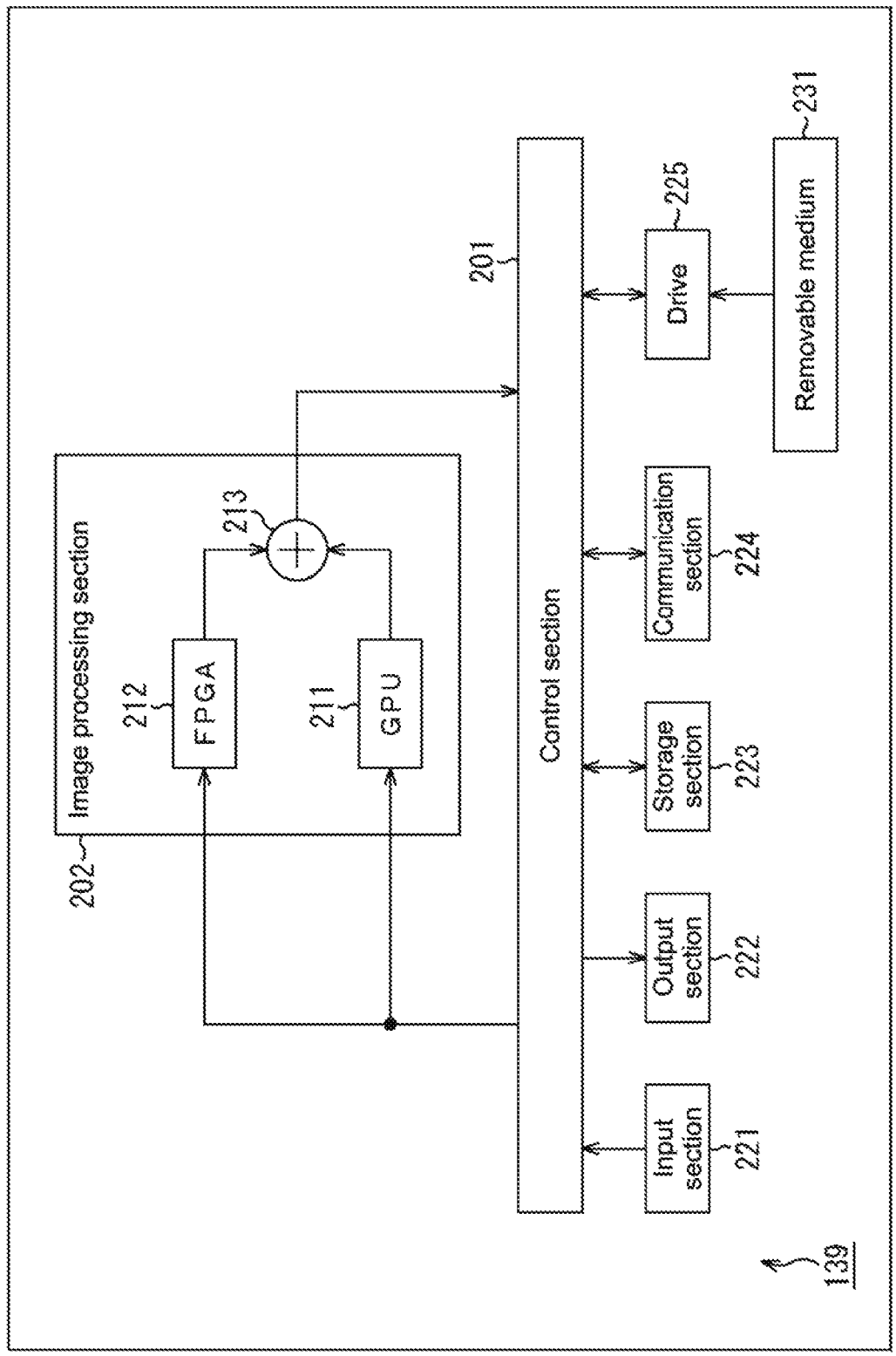
FIG. 2 is a block diagram of a main configuration example of a camera control section (CCU).

CCU FIG. 2 is a block diagram of a main configuration example of the CCU 139. As illustrated in FIG. 2, the CCU 139 includes a control section 201, an image processing section 202, an input section 221, an output section 222, a storage section 223, a communication section 224, and a drive 225.

The control section 201 performs arbitrary processing such as arithmetic processing or control processing. For example, the control section 201 performs processing regarding control of each processing section in the CCU 139. Further, for example, the control section 201 performs control regarding image processing for causing an image captured by the endoscope 101 (endoscopic image) to be displayed on (output to) the display device 141 instantly (in real time).

More specifically, for example, the control section 201 performs processing regarding distribution (allocation) of processing to devices (hardware resources) included in the image processing section 202. The processing to be distributed may be any processing, and may include, for example, processing regarding instant (real-time) output of medical data used in medical care. For example, the devices included in the image processing section (a plurality of assignable processing resources) include a plurality of CPU, GPU, and/or FPGA. The plurality of assignable processing resources may not be included in one device. For example, the plurality of assignable processing resources may include other devices or devices on the cloud.

Further, for example, the control section 201 performs processing regarding acquisition of information to be provided to the image processing section 202 or regarding provision of that information to the image processing section 202. This information may be any information and may include, for example, medical data used in medical care or the like. This medical data may be any information and may include, for example, a medical image (e.g., an endoscopic image of an affected part) used in medical care or the like. Further, the acquisition of information may include, for example, acquisition of information from the outside of the CCU 139 via the input section 221 or the communication section 224. For example, the control section 201 performs processing regarding acquisition of an image signal or the like of a medical image supplied from the camera head 105 via the communication section 224 or regarding provision of that image signal or the like to the image processing section 202.

Further, for example, the control section 201 performs processing regarding acquisition of information supplied from the image processing section 202 or regarding output of that information. This information may be any information and may include, for example, medical data (medical image). Further, the output of the information may include, for example, output to the outside of the CCU 139 via the output section 222 or the communication section 224. Further, for example, when the information is image information such as a medical image, the output of the information may include causing the display device 141 to display the image via the output section 222. Further, the output of the information may include causing the storage section 223 to store information or causing a removable medium 231 to record information via the drive 225.

The control section 201 has an arbitrary physical configuration. For example, the control section 201 may include dedicated hardware for a logic circuit such as a field programmable gate array (FPGA) or an application specific integrated circuit (ASIC) to achieve various types of processing by the hardware. Alternatively, the control section 201 may include general-purpose hardware including a CPU, a read only memory (ROM), a random access memory (RAM), and executes software by using them to achieve various types of processing.

The image processing section 202 is controlled by the control section 201 to perform processing regarding information supplied via the control section 201. For example, the image processing section 202 performs image processing on a medical image supplied from the control section 201. Further, for example, the image processing section 202 supplies information such as the medical image subjected to the image processing to the control section 201.

The image processing section 202 includes a plurality of arithmetic devices (arithmetic processing sections) as hardware resources, the arithmetic devices being physically separated from one another and each capable of performing processing independently. For example, the image processing section 202 may include a plurality of types of arithmetic processing sections as the plurality of arithmetic processing sections described above.

An item indicating the type of the arithmetic processing section may include, for example, at least one of a product serial number (ID), a use application, characteristics such as performance (capability) and a function, a physical structure, and the like. For example, the image processing section 202 may include a plurality of arithmetic processing sections having different product serial numbers (IDs). Further, for example, the image processing section 202 may include an arithmetic processing section for normal use and an arithmetic processing section for emergency use. Furthermore, for example, the image processing section 202 may include a plurality of arithmetic processing sections having different characteristics of processing capability. It should be noted that the characteristic of processing capability may be, for example, a characteristic regarding processing performance such as a processing speed and consumed power or may be, for example, a characteristic regarding a function such as executable processing. Furthermore, for example, the image processing section 202 may include a plurality of arithmetic processing sections having different physical configurations. As a matter of course, the items indicating the types of the arithmetic processing section are arbitrarily set and are not limited to those examples.

The image processing section 202 includes, as the plurality of types of the arithmetic processing sections, for example, a graphics processing unit (GPU) 211 and a field programmable gate array (FPGA) 212.

The GPU 211 is an arithmetic processing section including a configuration for image processing calculation. The GPU 211 has a characteristic having a strong point in image processing calculation and has a higher image processing arithmetic capability than the FPGA 212. To the contrary, the FPGA 212 is an arithmetic processing section including an integrated circuit capable of defining/changing an internal logic circuit by a user after production. The FPGA 212 has a characteristic capable of implementing arbitrary processing by programming and has higher general versatility than the GPU 211.

Further, when those resources are provided with redundancy, the GPU 211 is used for normal use, and the FPGA 212 is used for emergency use. In other words, the GPU 211 and the FPGA 212 are different from each other in use application and in characteristics of processing capability (characteristic regarding processing performance and characteristic regarding function). In other words, the GPU 211 and the FPGA 212 are different types of arithmetic processing sections.

It should be noted that the arithmetic processing sections of the image processing section 202 are not limited to the GPU 211 and FPGA 212 described above. For example, the image processing section 202 may include three or more arithmetic processing sections. In other words, the number of resources to which the processing is distributed may not be restrictive as long as the number is plural. Further, it is desirable that the FPGA 212 have a function of switching processing content in advance under the control of the control section 201.

The image processing section 202 further includes a combining processing section 213. The combining processing section 213 performs processing regarding combining of processing results of the GPU 211 and the FPGA 212 (e.g., generation of combined image). The combining processing section 213 then supplies information regarding a combining result to the control section 201. The control section 201 outputs information regarding the combining result to the outside of the CCU 139 (e.g., the display device 141) via, for example, the output section 222 or the communication section 224.

It should be noted that the GPU 211 or the FPGA 212 may perform processing regarding combining of processing results of the GPU 211 and the FPGA 212 (e.g., generation of combined image). In this case, the combining processing section 213 may be omitted. Further, a plurality of GPUs 211 may be provided.

The input section 221 includes an input device that receives information of the outside such as an input of the user. For example, the input section 221 may include a keyboard, a mouse, an operation button, a touch panel, a camera, a microphone, an input terminal, and the like. Further, the input section 221 may include various sensors such as an acceleration sensor, an optical sensor, and a temperature sensor, and input equipment such as a bar code reader. For example, the input section 221 receives information from the outside of the CCU 139 and supplies the received information to the control section 201.

The output section 222 includes an output device that outputs information such as images and sound. For example, the output section 222 may include a display, a speaker, an output terminal, and the like. For example, the output section 222 outputs information supplied from the control section 201 to the outside of the CCU 139.

The storage section 223 includes a storage medium that stores information such as a program or data. For example, the storage section 223 may include a hard disk, a RAM disk, a nonvolatile memory, and the like. The storage section 223 stores the information supplied from the control section 201 in the storage medium. Further, the storage section 223 supplies the information read from the storage medium to the control section 201.

The communication section 224 includes a communication device that performs communication of giving and receiving information such as a program or data to and from an external device via a predetermined communication medium (e.g., an arbitrary network such as the Internet). For example, the communication section 224 may include a network interface. For example, the communication section 224 performs communication (giving and receiving of a program or data) with a device on the outside of the CCU 139. It should be noted that the communication section 224 may have a wired communication function, a wireless communication function, or both of the communication functions.

The drive 225 reads information (program, data, etc.) stored in the removable medium 231 mounted thereto, such as a magnetic disk, an optical disc, a magneto-optical disk, or a semiconductor memory. The drive 225 supplies information read from the removable medium 231 to the control section 201. Further, in a case where a rewritable removable medium 231 is mounted to the drive 225, the drive 225 can cause the removable medium 231 to store information (program, data, etc.) supplied from the control section 201.

The control section 201 loads a program or the like stored in, for example, the storage section 223 and executes it, to perform various types of processing.

Functional Block

Figure 3:
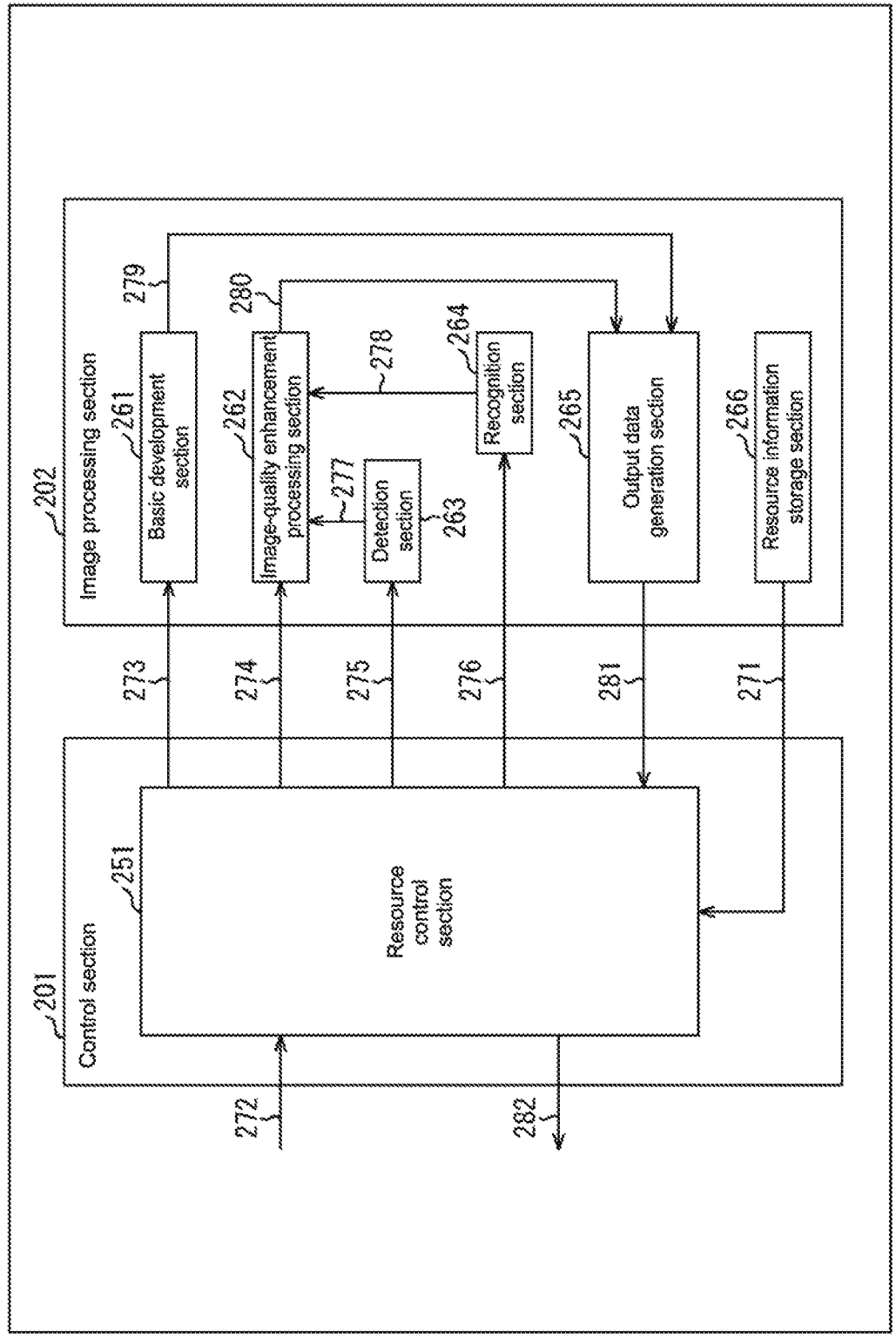
FIG. 3 is a functional block diagram for describing an example of a function achieved by the CCU.

The functions achieved by the above-mentioned hardware resources will be described. FIG. 3 illustrates an example of a functional block of functions achieved by the control section 201 and the image processing section 202. As illustrated in FIG. 3, the control section 201 achieves a resource control section 251.

The resource control section 251 performs processing regarding distribution of processing of instantly outputting medical data, and processing regarding provision of images to the image processing section 202, acquisition of images from the image processing section 202, and the like.

The image processing section 202 implements, using the arithmetic processing sections thereof, functions of a basic development section 261, an image-quality enhancement processing section 262, a detection section 263, a recognition section 264, an output data generation section 265, a resource information storage section 266, and the like.

The basic development section 261 performs processing regarding generation of captured images with usual image quality. For example, the basic development section 261 performs demosaic processing, conversion processing, and the like to convert raw data into captured images based on luminance or color difference. The image-quality enhancement processing section 262 performs processing regarding enhancement of the quality of images. For example, the image-quality enhancement processing section 262 performs super-resolution, noise reduction, and the like and generates captured images with higher quality than the captured images generated in the basic development section 261.

The detection section 263 performs processing regarding detection processing such as detection of bleeding. The recognition section 264 performs processing regarding recognition of a predetermined subject (e.g., the tip of forceps) in an image.

The output data generation section 265 performs processing regarding generation of output data that is output to the outside of the CCU 139. For example, the output data generation section 265 combines pieces of data (e.g., a plurality of captured images) generated in the basic development section 261 and the image-quality enhancement processing section 262 and generates a piece of output data.

The resource information storage section 266 stores resource information as information regarding the resources of the image processing section 202. The resource information may be any information and may include, for example, useful information in distributing the processing to the resources, such as processing capabilities, functions, and the like of the resources.

It should be noted that the resource information storage section 266 is allocated to, for example, each of the resources of the image processing section 202, for example, the GPU 211 and the FPGA 212. In other words, each of the resources of the image processing section 202 stores its own resource information. Therefore, in this case, the resource control section 251 accesses each of the resources of the image processing section 202 and acquires the resource information from each resource.

It should be noted that the resource information storage section 266 may be formed in a resource other than the resources such as the GPU 211, the FPGA 212, and the like of the image processing section 202. In such a case, the resource control section 251 may access the resource information storage section 266 provided at a position different from the resources within the image processing section 202 and acquire resource information of each resource.

Further, the resource information storage section 266 may be formed in the storage section 223 in advance.

The resource control section 251 allocates each process for achieving the functions exerted by, for example, the basic development section 261 to the recognition section 264 to the resources of the image processing section 202 (e.g., the GPU 211 and the FPGA 212).

For example, the resource control section 251 distributes (allocates) processing regarding instant output of medical data to each of the resources of the image processing section 202. This allows the resource control section 251 to perform the processing by using the plurality of resources, thus improving the utilization efficiency of the resources.

Further, the resource control section 251 adaptively distributes the processing regarding instant output of medical data to a plurality of types of resources as well. Therefore, the resource control section 251 can suppress reduction in the utilization efficiency of the plurality of types of resources.

Furthermore, the resource control section 251 distributes (allocates) the processing on the basis of the content of the processing to be distributed and the performance of the resources. Therefore, the resource control section 251 can distribute the processing more suitably and improve the utilization efficiency of the resources.

It should be noted that the resource control section 251 can grasp the performance of the resources to which the processing is distributed, from the resource information, as described above.

Example of Processing Distribution

Next, the processing distribution to the resources will be described. For example, in medical care equipment, as in a medical image 301 illustrated in A of FIG. 4, the GPU 211 performs image processing for presentation to a surgeon, and the FPGA 212 also performs image processing in preparation for the failure of the GPU 211 frequently. In this case, when the GPU 211 processes the entire image, this is computationally expensive. Thus, the processing at low computational costs and with reduced image quality is performed.

In this regard, the resource control section 251 determines, for a region of interest (ROI) specified by the surgeon, the ROI size within the frame that is allowable for the processing capability of the GPU 211. The resource control section 251 gives an instruction to cause the GPU 211 to perform image-quality enhancement processing only on the ROI and also gives an instruction to cause the FPGA 212 to perform basic image processing on the part other than the ROI. This resource control provides the medical image 301 illustrated in, for example, B of FIG. 4. In this medical image 301, a region of interest 302 enclosed by a dotted line 302*a* is provided with a higher quality than the other regions. In other words, the surgeon can perform the procedure by using the image with higher visibility. This makes the surgery procedure more efficient.

It should be noted that changing the image processing only for a particular region within the frame in this manner has concerns about an uncomfortable feeling at the boundary between the region where the image processing is performed and the region where the image processing is not performed, or about misdiagnoses. Therefore, the boundary part (dotted line 302*a*) may be clarified to the surgeon with display of a visual indication such as a dotted line or the like.

It should be noted that the expression of the boundary part by the image processing may be changed depending on the processing. Changing the number, color, type, thickness, and shape of frame borders of the boundary part depending on processing content or a processing status allows presentation of the processing content or the processing status to the user without interrupting the surgery procedure. For example, as illustrated in B of FIG. 4, the presence or absence of delay caused after the image-quality enhancement processing may be expressed by the number of frame borders indicating the boundary between a region of interest and the other region. This allows the presence or absence of delay to be intuitively presented to the user.

Figure 4:
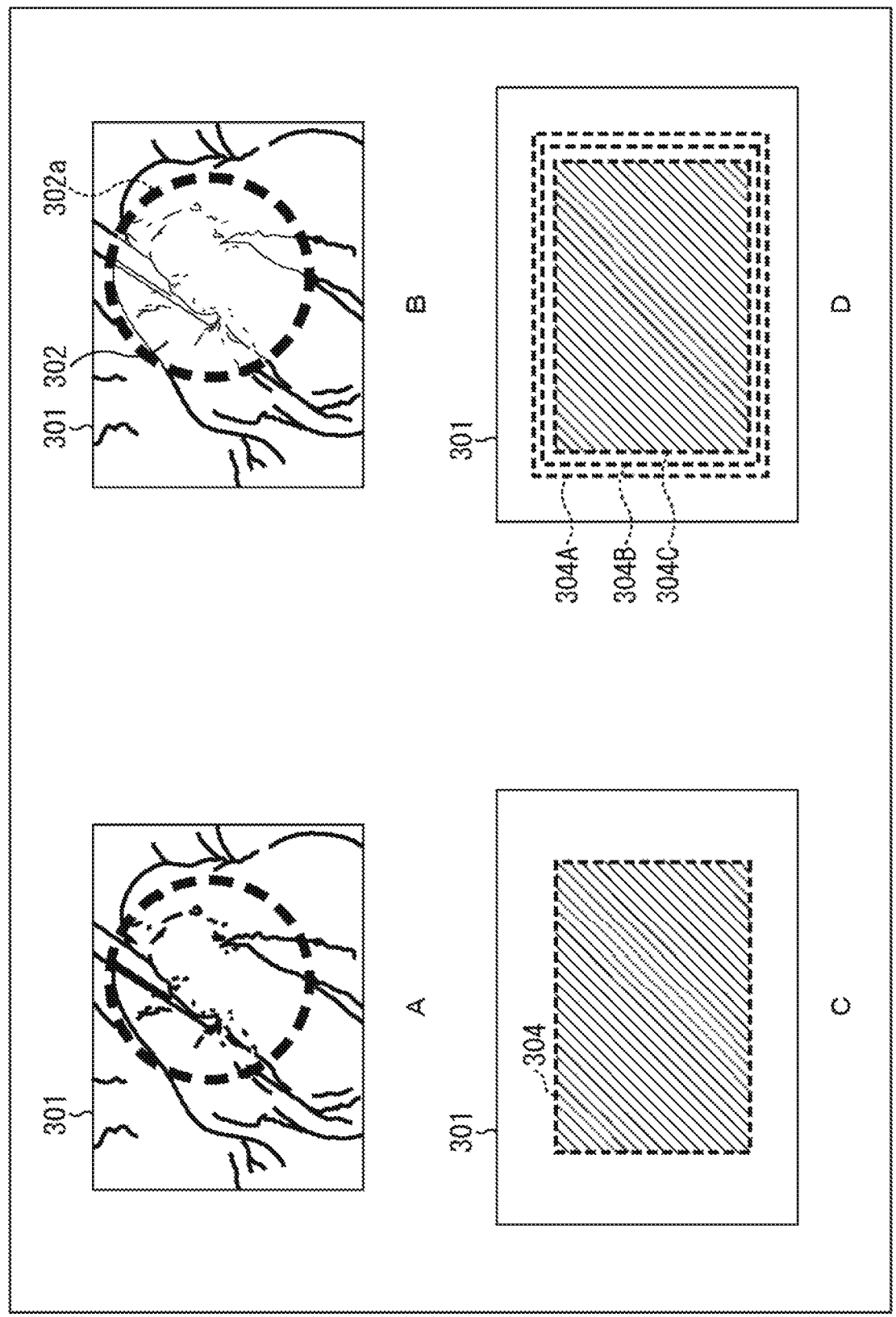
FIG. 4 is a diagram for describing examples of image processing.

For example, in a case where the delay is not caused by the image-quality enhancement processing (in a case where the amount of delay is not larger than a predetermined constant value), as in the medical image 301 illustrated in C of FIG. 4, the boundary between the region of interest, which is hatched, and the other region is indicated by a frame border 304 of a single dotted line. In a case where the delay is caused by the image-quality enhancement processing (in a case where the amount of delay is larger than a predetermined constant value), as in the medical image 301 illustrated in D of FIG. 4, the boundary between the region of interest and the other region is indicated by three dotted lines of a frame border 304A to a frame border 304C. In such a manner, the user can intuitively grasp the presence or absence of delay on the basis of the number of frame borders.

It should be noted that the number of frame borders may be determined depending on the magnification of the amount of delay. For example, in a case where the delay does not occur, the boundary between the hatched region of interest and the other region may be expressed by a single frame border, and as the amount of delay increases, the number of frame borders may increase. This allows the amount of delay to be intuitively presented to the user. In addition thereto, if the transmission quality is good, the frame border is displayed in green, and if the quality is poor (e.g., in a case where a packet loss rate is larger than a constant value during transmission), the frame border is displayed in red. In such a manner, the user can be intuitively notified of image degradation or a high risk of processing interruption.

Further, in a case where the processing is distributed to a resource on the outside of the CCU, which will be described later, the thickness of the frame border (visual indication) or the number of frame borders may be changed depending on an available occupancy time for an external resource, an operating time, and an incurred expense. For example, the number of frame borders is reduced as the available occupancy time for an external resource decreases. This allows the user to intuitively grasp an available time. Further, if an incurred expense generated by use of an external resource is within a budget, the frame border is displayed in green. If the incurred expense approaches the limit of the budget, the frame border is displayed in yellow. If the incurred expense exceeds the budget, the frame border is displayed in red. Thus, the user can intuitively grasp a status of the incurred expense.

Furthermore, in a case where a diagnosis support function of supporting the discovery of a lesion by machine learning is used, a configuration in which the frame border (visual indication) is changed when a lesion is discovered may be provided. For example, when a video of the endoscope is analyzed in real time by a technique using machine learning, a frame border of a boundary part indicating a range to which the analysis is applied is displayed. If a region determined as a lesion at a certain probability or more is present within the screen, the frame border is displayed in red. This allows the user to intuitively grasp whether a lesion is detected or not without moving the line of sight between a screen displaying diagnosis support results and a screen displaying a real-time video of the endoscope. It should be noted that a method satisfying necessary degree of accuracy, such as a deep neural network or reinforcement learning, is appropriately used for the machine learning.

It should be noted that the boundary part may be expressed by causing the frame border to blink or by changing the transmittance or brightness of the frame border according to the processing content or the processing status of the image processing. For example, when the frame border is red, it may be difficult to distinguish the frame border from the color of a biological tissue. Thus, the color of the frame border is changed on the basis of a color distribution of the image. Further, when the diagnosis support function is used, if a lesion is detected, the transmittance of the color of the frame border may be changed to be easily visible by the user.

Distribution Range of Resources

It should be noted that the region of interest (ROI) may be set by an arbitrary method. For example, as described above, the surgeon or the like may specify the ROI, but other methods may be performed.

For example, the CCU 139 may set a predetermined region (e.g., vicinity of the center of an image capture range), which is likely to be a region of interest of the surgeon, as a region of interest without inputs of the surgeon. Further, for example, the CCU 139 may set the center region of the screen where vignetting of the rigid endoscope is not generated, as a region of interest, without inputs of the surgeon.

Further, for example, the CCU 139 may set, as a region of interest, a near-field region including a predetermined subject (e.g., the tip of forceps) detected by a recognition technique or the like of the recognition section 264.

Further, for example, the CCU 139 may set a high spatial frequency region or low spatial frequency region as a region of interest.

Hereinabove, the resources to which the processing is allocated are changed in the region of interest and the other region. In addition thereto, for example, the CCU 139 may change the resources, to which the processing is allocated, on a line basis within the frame as in interlaced display.

Further, for example, in a case where the endoscope 101 captures images with white light and IR light (ICG imaging) by a frame sequential method, because of monochrome ICG images, it is unnecessary to perform color-related processing unlike color images. In this regard, for example, the CCU 139 may change the resources, to which the processing is allocated, on a frame basis. In such a manner, a resource for which the color-related processing is omitted is generated, so that the surplus computational resource may be distributed to white light image processing.

Further, for example, the CCU 139 may change the resources, to which the processing is allocated, in a high temporal frequency region and a low temporal frequency region.

Distribution Processing of Resources

Further, the Example of Processing Distribution has described the example in which the resources to which the processing is allocated are changed in the image-quality enhancement processing for a region of interest and the basic image processing for the other region. However, how to distribute the resources (allocation of each process to resource) is arbitrarily determined, and is not limited to this example.

For example, the image-quality enhancement processing for a region of interest and detection processing such as detection of bleeding for the other region may be allocated to different resources. Further, for example, processing of improving distinguishability (highlighting of a blood vessel, displaying of blood vessel depth, etc.) for the region of interest and the basic development processing for the other region may be allocated to different resources. Furthermore, for example, processing of improving moving image visibility (e.g., frame interpolation processing for interpolating frames from 30 fps to 60 fps, or from 60 fps to 120 fps) for the region of interest and the basic development processing for the other region may be allocated to different resources.

As described above, since adaptive distribution is performed for processing to be distributed, the resource control section 251 can perform distribution of the processing more suitably and can improve the utilization efficiency of the resources.

Resource Control Protocol

The Example of Processing Distribution has described that the change of the resources is mainly performed depending on the arithmetic processing capability. In other words, processing that needs complicated, high-speed parallel computation is allocated to the GPU 211, and fixed processing independent of data is allocated to the FPGA 212. However, how to distribute the processing is not limited to this example. For example, the following information may be received as resource information, and the resources may be allocated thereto depending on the situation.

Arithmetic performance: This shows number of times of computation per unit time. For example, high-load processing may be allocated to a resource having high arithmetic performance, which can stand the load.

Consumed power: For example, in consideration of tolerable total power of the entire system, the processing may be allocated to an available resource.

Response speed: For example, for a region where the processing delay is negligible, such as a region other than the region of interest, a resource having a high processing capability but having a poor response speed, such as cloud, may be selected.

Availability of occupancy: For example, it is necessary to hold the same image processing for a certain time depending on the surgery procedure. In this case, a resource may be selected in consideration of the availability of occupancy and an available occupancy time.

Cumulative operating time: For example, a resource to be used may be selected in consideration of a product life.

HW version: Depending on hardware (HW), requested image processing may not be performed. In consideration of the hardware version, a resource may be selected (i.e., a resource that can execute the processing may be selected).

Usage fee: In a case where the user is charged per use of a resource or per operating time, a resource may be selected in consideration of the usage fee and the user's set budget.

For example, the resource control section 251 receives the resource information including the information described above from each resource and determines a resource to be selected. After the determination, the resource control section 251 notifies each resource of an occupancy time, an occupancy arithmetic capability, signal processing to be performed, and the like.

Trigger of Resource Control

A trigger of the resource control may be arbitrary and is not limited to the above-mentioned ROI setting by the surgeon. For example, in a case where forceps is recognized by a recognition technique or the like and where the tip of the forceps is in an image, detection of a region including that tip may be set as a trigger. In such a case, a region including the detected tip may be set as a ROI to perform resource control. Further, the resource control may be performed with switching between image capture modes as a trigger.

Flow of Image Processing

Figure 5:
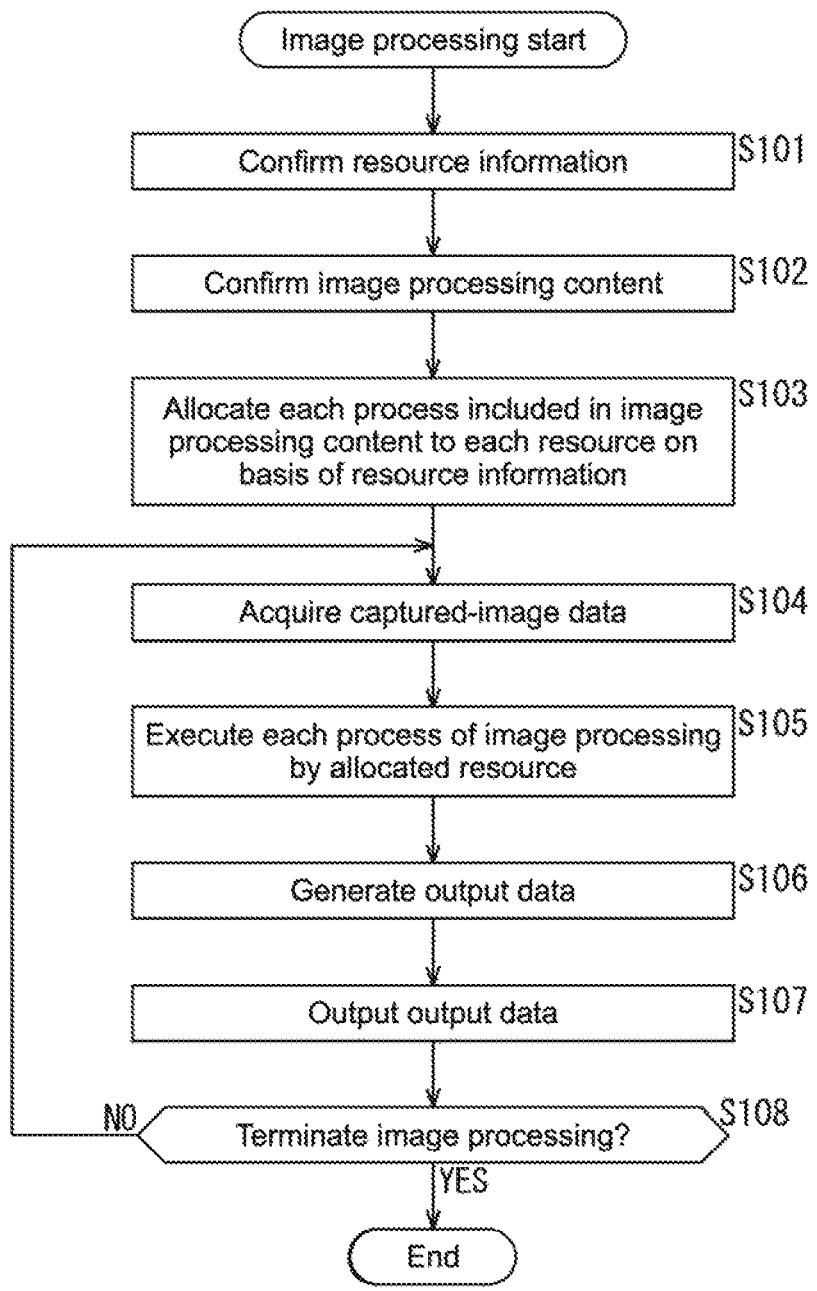
FIG. 5 is a flowchart for describing an example of a flow of the image processing.

Next, an example of a flow of the image processing executed by the CCU 139 will be described with reference to a flowchart of FIG. 5.

When the image processing is started, in Step S101, the resource control section 251 acquires resource information from the resource information storage section 266 (arrow 271 of FIG. 3) and confirms the resource information. In Step S102, the resource control section 251 confirms image processing content to be allocated. In Step S103, the resource control section 251 allocates each process included in the image processing content to each of the resources on the basis of the resource information.

In Step S104, the resource control section 251 acquires captured-image data (endoscopic image) supplied from the endoscope 101 via the communication section 224, for example (arrow 272). In Step S105, the resource control section 251 supplies necessary information such as the captured-image data to the resources allocated in Step S103 (arrow 273 to arrow 276) and cause the resources to execute the respective processes. Each of the resources executes the process allocated by the resource control section 251 by using the supplied information.

For example, when the detection section 263 performs detection processing, the detection section 263 supplies a processing result to the image-quality enhancement processing section 262 (arrow 277). Further, for example, when the recognition section 264 performs processing, the recognition section 264 supplies a processing result to the image-quality enhancement processing section 262 (arrow 278). When the basic development section 261 performs basic development processing, the basic development section 261 supplies a processing result to the output data generation section 265 (arrow 279). Further, when the image-quality enhancement processing section 262 performs image-quality enhancement processing, the image-quality enhancement processing section 262 supplies a processing result to the output data generation section 265 (arrow 280).

In Step S106, the resource control section 251 causes the output data generation section 265 to generate output data. Under the control of the resource control section 251, the output data generation section 265 combines, for example, the result of the basic development processing and the result of the image-quality enhancement processing, to generate output data. The output data generation section 265 supplies the generated output data to the resource control section 251 (arrow 281).

In Step S107, the resource control section 251 outputs the output data to the outside of the CCU 139 (arrow 282). For example, the resource control section 251 supplies the output data to the display device 141 via the output section 222, so that the endoscopic image or the like included in the output data is displayed thereon.

In Step S108, the resource control section 251 determines whether to terminate the image processing. For example, when it is determined that the image processing is not terminated because the surgery is not completed, the processing returns to Step S104 and repeats the processing of Step S104 and the processing subsequent thereto. In other words, until the image processing is terminated, the processing of Step S104 to Step S108 is repeatedly executed.

For example, when the surgery is completed and it is determined that the image processing is terminated in Step S108, the image processing is terminated.

When the image processing is performed as described above, the processing regarding instant output of medical data can be adaptively distributed to the plurality of arithmetic processing sections, to thus improve the utilization efficiency of the resources. For example, a high-quality endoscopic image, which is difficult to achieve by a single arithmetic processing section, can be provided to the surgeon. This allows the surgeon to improve the efficiency of the surgery procedure. Further, since the arithmetic resources can be adaptively distributed as described above, it becomes unnecessary to provide the single CCU 139 with high arithmetic performance. This can provide a highly functional service to the user at low device costs.

Further, for example, in a case where the resource control section 251 of the FPGA performs distribution processing for a plurality of GPUs 211 each of which is the image processing section 202, the processing content is changed for each GPU 211. Thus, high arithmetic performance, which is difficult to obtain by a single GPU 211, can be achieved. At that time, that following configuration may be provided, in which processing results output from the plurality of GPUs 211 are input to the FPGA (resource control section 251) again, and the FPGA combines those processing results for output.

3. Second Embodiment

CCU System

It should be noted that a resource to which the processing is distributed may be out of the CCU 139. For example, the CCU 139 of FIG. 1 may include a plurality of CCUs 139 (i.e., configured as CCU system).

Figure 6:
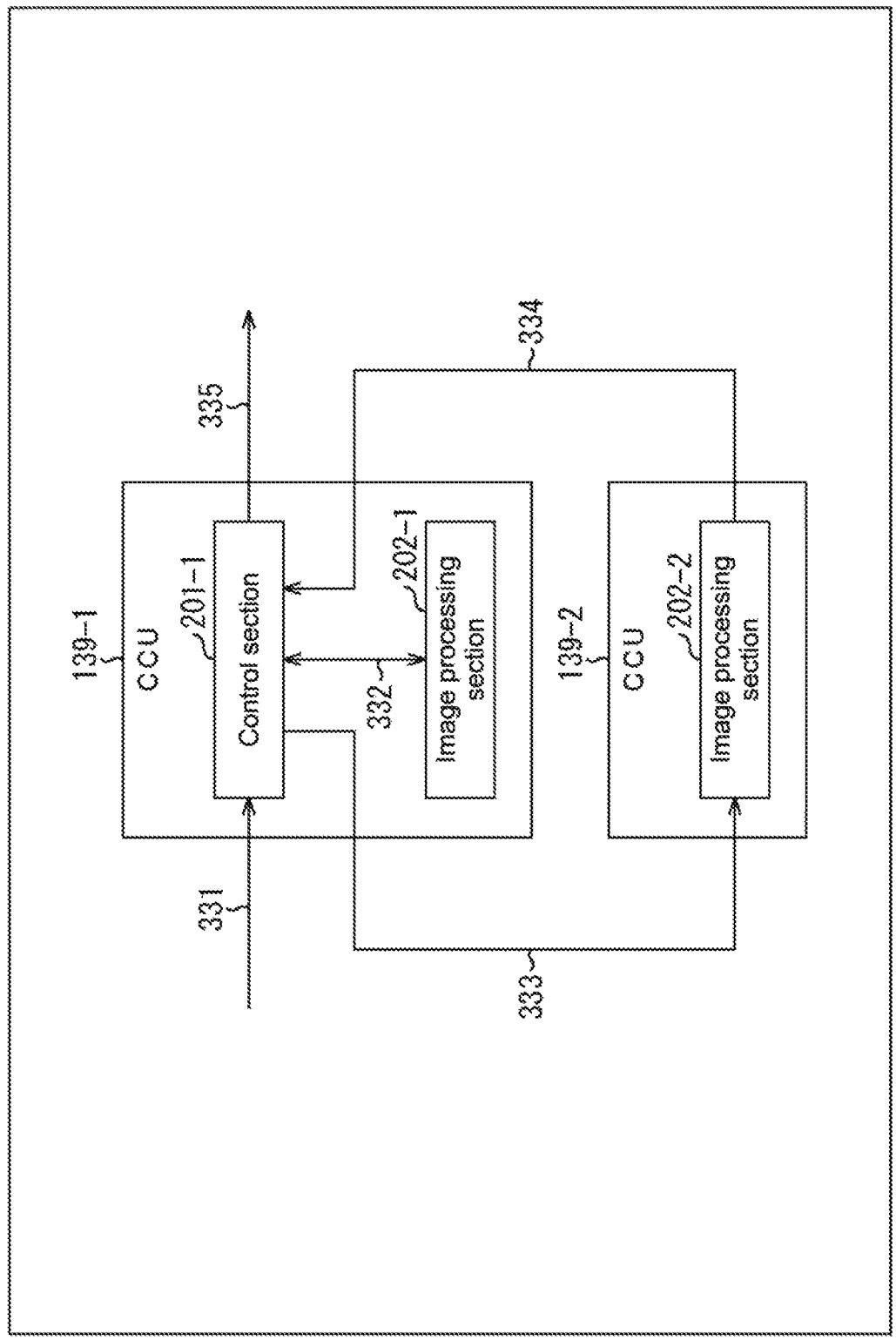
FIG. 6 is a block diagram of a main configuration example of a CCU system.

FIG. 6 is a block diagram showing a main configuration example of a CCU system (corresponding to the CCU 139 of FIG. 1) in the above case.

The CCU system illustrated in FIG. 6 includes two CCUs 139 (CCU 139-1 and CCU 139-2). Each of the CCU 139-1 and the CCU 139-2 is a device basically identical to the CCU 139 described in the first embodiment, and each have an identical configuration. As in the case of the first embodiment, the CCU 139-1 is connected with the endoscope 101 and the display device 141 via a wired or wireless transmission path, and is configured to be capable of giving and receiving information via the transmission path. It should be noted that the CCU 139-2 is also connected to the CCU 139-1 so as to be capable of communication. The CCU 139-1 and the CCU 139-2 performs communication via the respective communication sections 224. This communication is performed via a wired or wireless communication medium.

It should be noted that each of the CCU 139-1 and the CCU 139-2 has the configuration described with reference to FIG. 2, but FIG. 6 illustrates a partial functional block thereof.

In the case of the CCU system of FIG. 6, the CCU 139-1 (camera controller), which is one of the plurality of CCUs 139 forming the CCU system, is a main resource and performs processing distribution. In other words, a control section 201-1 of the CCU 139-1 performs the processing distribution. This processing distribution is substantially similar to that described in the first embodiment. However, in this embodiment, the resources of the plurality of CCUs 139 are processing distribution targets. In other words, in the case of FIG. 6, the control section 201-1 of the CCU 139-1 adaptively distributes the processing not only to the resources of the image processing section 202-1 but also to resources of an image processing section 202-2 of the CCU 139-2.

In other words, an image signal or the like transmitted from the endoscope 101 is supplied to the control section 201-1 of the CCU 139-1 (via the communication section 224) (arrow 331). The control section 201-1 distributes the processing to the image processing section 202-1 and the image processing section 202-2 of the CCU 139-2 as an external resource on the basis of the processing content and resource information of them (arrow 332 and arrow 333). The image processing section 202-1 and the image processing section 202-2 each execute processing allocated thereto.

The image processing section 202-2 supplies a processing result to the image processing section 202-1 via the control section 201-1 (arrow 334 and arrow 332). The image processing section 202-1 combines a processing result thereof and the processing result of the image processing section 202-2, generates output data, and outputs the output data to, for example, the display device 141 via the control section 201-1 (arrow 332 and arrow 335). On the display device 141, an endoscopic image or the like included in that output data is displayed.

It should be noted that the CCU 139-2 as an external resource may be configured as any hardware. For example, the CCU 139-2 may be provided to the endoscopic surgery system 100 to which the CCU 139-1 belongs, so as to be a backup device or the like of the CCU 139-1 as a main resource. Further, for example, the CCU 139-2 may belong to an endoscopic surgery system 100 that is different from the endoscopic surgery system 100 to which the CCU 139-1 belongs. In such a case, the endoscopic surgery system 100 to which the CCU 139-1 belongs and the endoscopic surgery system 100 to which the CCU 139-2 belongs may be provided in an identical surgery room. For example, the endoscopic surgery system 100 to which the CCU 139-2 belongs may be provided as a backup system of the endoscopic surgery system 100 to which the CCU 139-1 belongs.

Furthermore, the endoscopic surgery system 100 to which the CCU 139-1 belongs and the endoscopic surgery system 100 to which the CCU 139-2 belongs may be provided in different surgery rooms. For example, in normal times, the endoscopic surgery system 100 to which the CCU 139-1 belongs and the endoscopic surgery system 100 to which the CCU 139-2 belongs are used in different surgery rooms. However, in a case where the endoscopic surgery system 100 to which the CCU 139-2 belongs is not utilized, the CCU 139-1 may be allowed to use the resources of the CCU 139-2.

Furthermore, the endoscopic surgery system 100 to which the CCU 139-1 belongs and the endoscopic surgery system 100 to which the CCU 139-2 belongs may be provided in different hospitals or the like.

As a matter of course, the CCU 139-2 may belong to a system other than the endoscopic surgery system described above. Further, a device as an external resource may be any device and may not be the CCU 139, as long as it has a configuration capable of executing allocated processing (i.e., includes a resource to which the processing is allocated) and capable of performing communication with another device. It should be noted that as in the example of FIG. 6, if the main resource and the external resource are devices having a similar configuration to perform similar processing, control can be performed more easily.

It should be noted that the number of external resources is arbitrary and may be two or more (multiple). For example, the above-mentioned CCU unit may include three or more CCUs 139. The number of arithmetic processing sections of each CCU 139 may be unified or not unified.

Functional Block

Figure 7:
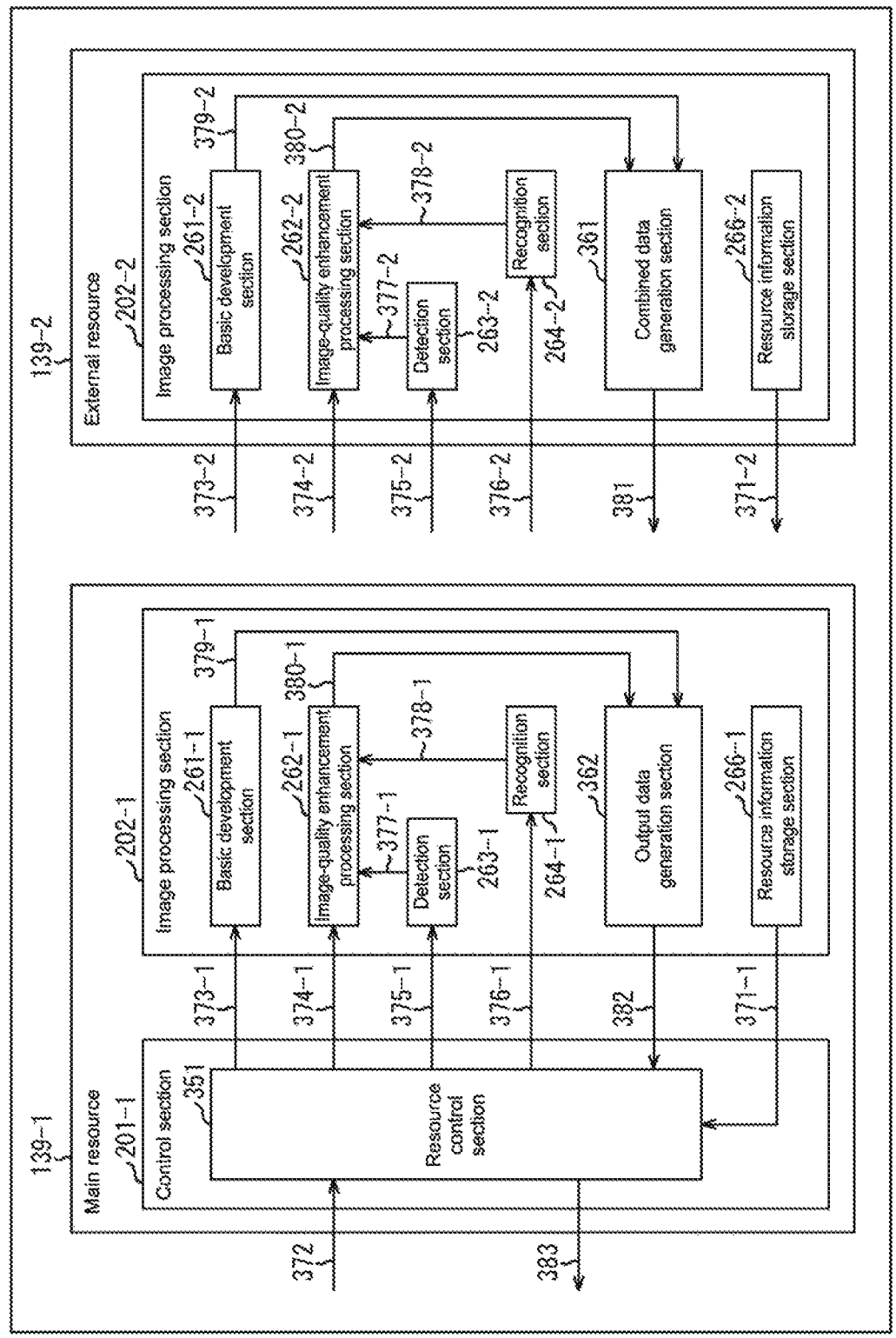
FIG. 7 is a functional block diagram for describing an example of a function achieved by the CCU system.

The functions achieved by the above-mentioned hardware resources will be described. FIG. 7 illustrates an example of a functional block of functions achieved by the control section 201-1, the image processing section 202-1, and the image processing section 202-2. As illustrated in FIG. 7, the control section 201-1 achieves a resource control section 351.

The resource control section 351 basically has a configuration similar to that of the resource control section 251 and performs processing similar thereto, but the resource control section 351 distributes the processing not only to the image processing section 202-1 of the main resource but also to the image processing section 202-2 of the CCU 139-2 as an external resource. In other words, the resource control section 351 is configured to adaptively distribute processing regarding instant output of medical data to the image processing section 202-1 and the image processing section 202-2.

The image processing section 202-2 of the CCU 139-2 as an external resource basically has a configuration similar to that of the image processing section 202 (FIG. 3), but includes a combined data generation section 361 instead of the output data generation section 265.

The combined data generation section 361 performs processing regarding generation of combined data that is output to the outside of the CCU 139-2. For example, the combined data generation section 361 combines pieces of data (e.g., a plurality of captured images) generated in a basic development section 261-2 and an image-quality enhancement processing section 262-2, and generates a piece of combined data. The combined data generation section 361 supplies the combined data to the image processing section 202-1 (output data generation section 362) via the resource control section 351.

It should be noted that, though not illustrated in FIG. 7, arrows 371-2, 373-2 to 376-2, and 381 are connected to the resource control section 351.

The image processing section 202-1 of the CCU 139-1 as a main resource basically has a configuration similar to that of the image processing section 202 (FIG. 3), but includes an output data generation section 362 instead of the output data generation section 265.

The output data generation section 362 performs processing regarding generation of output data that is output to the outside of the CCU 139-1. For example, the output data generation section 362 combines pieces of data (e.g., a plurality of captured images) generated in a basic development section 261-1 and an image-quality enhancement processing section 262-1, and the combined data supplied from the combined data generation section 361 via the resource control section 351, to generate a piece of output data. The output data generation section 362 outputs the output data to the outside of the CCU 139-1 (e.g., the display device 141) via the resource control section 351, the output section 222, and the like.

The resource control section 351 distributes (allocates) the processing regarding instant output of medical data not only to the resources of the image processing section 202-1 but also to the resources of the image processing section 202-2. This allows the resource control section 351 to perform the processing by using the plurality of resources as in the case of the first embodiment, thus improving the utilization efficiency of the resources.

Flow of Image Processing

Figure 8:
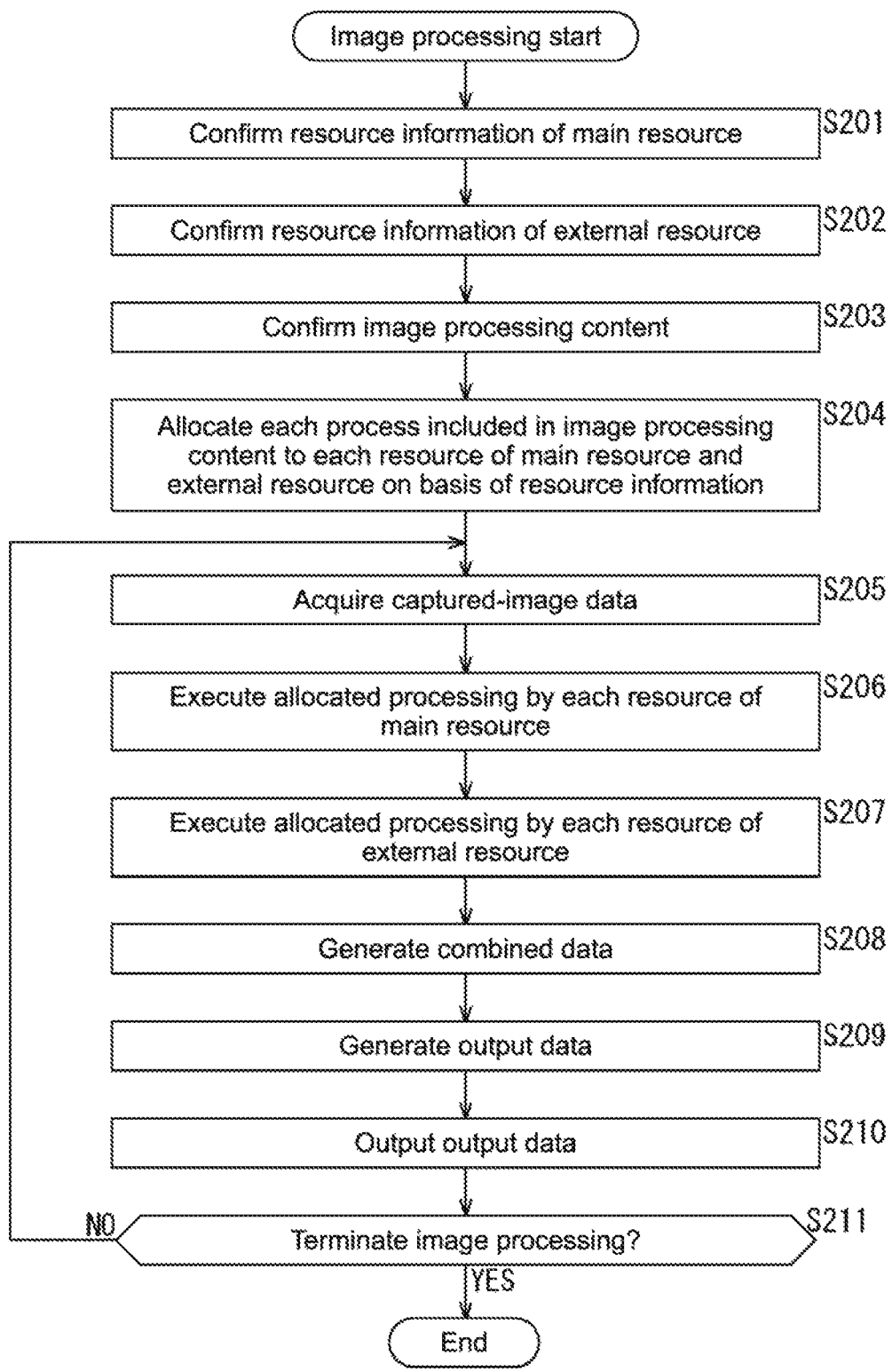
FIG. 8 is a flowchart for describing an example of a flow of image processing.

Next, an example of a flow of the image processing in this case will be described with reference to a flowchart of FIG. 8.

When the image processing is started, in Step S201, the resource control section 351 acquires resource information of the main resource (CCU 139-1) from a resource information storage section 266-1 and confirms the resource information (arrow 371-1). Similarly, in Step S202, the resource control section 351 acquires resource information of the external resource (CCU 139-2) from a resource information storage section 266-2 and confirms the resource information (arrow 371-2).

In Step S203, the resource control section 351 confirms image processing content to be allocated. In Step S204, the resource control section 351 allocates each process included in the image processing content to each of the resources of the main resource and the external resource on the basis of the resource information.

In Step S205, the resource control section 351 acquires captured-image data (endoscopic image) supplied from the endoscope 101 via the communication section 224, for example (arrow 372). In Step S206, the resource control section 351 supplies necessary information such as the captured-image data to the resources of the main resource that are allocated in Step S204 (arrow 373-1 to arrow 376-1) and causes the resources to execute the respective processes. Each of the resources executes the process allocated by the resource control section 351 by using the supplied information.

For example, when a detection section 263-1 performs detection processing, the detection section 263-1 supplies a processing result to the image-quality enhancement processing section 262-1 (arrow 377-1). Further, for example, when a recognition section 264-1 performs processing, the recognition section 264-1 supplies a processing result to the image-quality enhancement processing section 262-1 (arrow 378-1). When the basic development section 261-1 performs basic development processing, the basic development section 261-1 supplies a processing result to the output data generation section 362 (arrow 379-1). Further, when the image-quality enhancement processing section 262-1 performs image-quality enhancement processing, the image-quality enhancement processing section 262-1 supplies a processing result to the output data generation section 362 (arrow 380-1).

Similarly, in Step S207, the resource control section 351 supplies necessary information such as the captured-image data to the resources of the external resource that are allocated in Step S204 (arrow 373-2 to arrow 376-2) and causes the resources to execute the respective processes. Each of the resources executes the process allocated by the resource control section 351 by using the supplied information.

For example, when a detection section 263-2 performs detection processing, the detection section 263-2 supplies a processing result to the image-quality enhancement processing section 262-2 (arrow 377-2). Further, for example, when a recognition section 264-2 performs processing, the recognition section 264-2 supplies a processing result to the image-quality enhancement processing section 262-2 (arrow 378-2). When the basic development section 261-2 performs basic development processing, the basic development section 261-2 supplies a processing result to the combined data generation section 361 (arrow 379-2). Further, when the image-quality enhancement processing section 262-2 performs image-quality enhancement processing, the image-quality enhancement processing section 262-2 supplies a processing result to the combined data generation section 361 (arrow 380-2).

In Step S208, the resource control section 351 causes the combined data generation section 361 to generate combined data. Under the control of the resource control section 351, the combined data generation section 361 combines the result of the basic development processing and the result of the image-quality enhancement processing, for example, to generate combined data. The combined data generation section 361 supplies the generated combined data to the output data generation section 362 via the resource control section 351 (arrow 381 and arrow 382).

In Step S209, the resource control section 351 causes the output data generation section 362 to generate output data. Under the control of the resource control section 351, the output data generation section 362 combines, for example, the results of the basic development processing and the image-quality enhancement processing and the combined data, to generate output data. The output data generation section 362 supplies the generated output data to the resource control section 351 (arrow 382).

In Step S210, the resource control section 351 outputs the output data to the outside of the CCU 139-1 (arrow 383). For example, the resource control section 351 supplies the output data to the display device 141 via the output section 222, so that the endoscopic image or the like included in the output data is displayed thereon.

In Step S211, the resource control section 351 determines whether to terminate the image processing. For example, when it is determined that the image processing is not terminated because the surgery is not completed, the processing returns to Step S205 and repeats the processing of Step S205 and the processing subsequent thereto. In other words, until the image processing is terminated, the processing of Step S205 to Step S211 is repeatedly executed.

For example, when the surgery is completed and it is determined that the image processing is terminated in Step S211, the image processing is terminated.

When the image processing is performed as described above, the processing regarding instant output of medical data can be adaptively distributed to the plurality of arithmetic processing sections, to thus improve the utilization efficiency of the resources. For example, a high-quality endoscopic image, which is difficult to achieve by the single CCU 139, can be provided to the surgeon. This allows the surgeon to improve the efficiency of the surgery procedure. Further, since the arithmetic resources can be adaptively distributed as described above, it becomes unnecessary to provide the single CCU 139 with high arithmetic performance. This can provide a highly functional service to the user at low device costs.

4. Third Embodiment

CCU System

Figure 9:
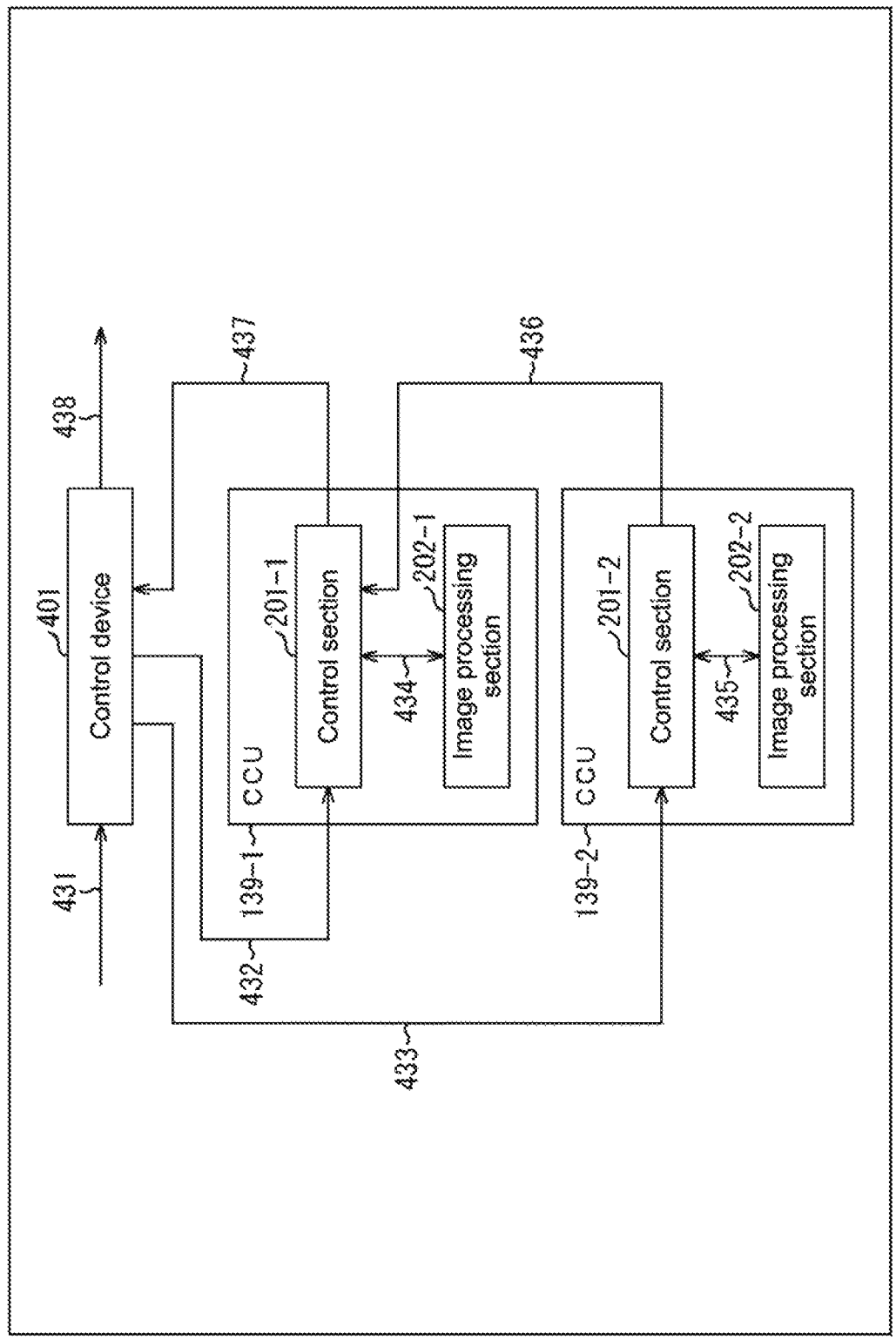
FIG. 9 is a block diagram of another configuration example of the CCU system.

Further, the control may be performed on the outside of each CCU 139. FIG. 9 illustrates a main configuration example of a CCU system (corresponding to the CCU 139 of FIG. 1) in such a case.

The CCU system illustrated in FIG. 9 includes two CCUs 139 (CCU 139-1 and CCU 139-2) as in the second embodiment. In this embodiment, however, the CCU system further includes a control device 401. It should be noted that each of the CCU 139-1 and the CCU 139-2 is a device basically identical to the CCU 139 described in the first embodiment, and each have an identical configuration. It should be noted that FIG. 9 illustrates only a partial functional block of the CCU 139-1 and the CCU 139-2.

The endoscope 101 and the display device 141 are connected to the control device 401. The control device 401 performs processing of distributing the processing of the CCU 139-1 and the CCU 139-2, for example. It should be noted that processing distribution to the resources of the image processing section 202-1 within the CCU 139-1 is performed by the control section 201-1 of the CCU 139-1. Similarly, processing distribution to the resources of the image processing section 202-2 within the CCU 139-2 is performed by the control section 201-2 of the CCU 139-2.

For example, an image signal or the like transmitted from the endoscope 101 is supplied to the control device 401 (arrow 431). The control device 401 distributes the processing to each of the CCU 139-1 and the CCU 139-2 on the basis of the processing content and resource information of them (arrow 432 and arrow 433). The control section 201-1 of the CCU 139-1 distributes the processing to the image processing section 202-1 on the basis of the processing content and the resource information (arrow 434). Similarly, the control section 201-2 of the CCU 139-2 distributes the processing to the image processing section 202-2 on the basis of the processing content and the resource information (arrow 435).

The image processing section 202-1 and the image processing section 202-2 each execute processing allocated thereto. The image processing section 202-2 supplies a processing result to the control section 201-2 and the image processing section 202-1 via the control section 201-1 (arrow 435, arrow 436, and arrow 434). The image processing section 202-1 combines a processing result thereof and the processing result of the image processing section 202-2, generates output data, and outputs the output data to, for example, the display device 141 via the control section 201-1 and the control device 401 (arrow 434, arrow 437, and arrow 438). On the display device 141, an endoscopic image or the like included in that output data is displayed.

It should be noted that the CCU 139-1 and the CCU 139-2 may be configured as any hardware. For example, the CCU 139-2 may be provided to the endoscopic surgery system 100 to which the CCU 139-1 belongs, so as to be a backup device or the like of the CCU 139-1. In such a case, the control device 401 may also belong to that endoscopic surgery system 100 or may be configured as a device that does not belong to the endoscopic surgery system 100. For example, the control device 401 may be configured as a device that controls the endoscopic surgery system 100.

Further, for example, the CCU 139-1 and the CCU 139-2 may belong to different endoscopic surgery systems 100. In such a case, the endoscopic surgery system 100 to which the CCU 139-1 belongs and the endoscopic surgery system 100 to which the CCU 139-2 belongs may be provided in an identical surgery room. For example, the endoscopic surgery system 100 to which the CCU 139-2 belongs may be provided as a backup system of the endoscopic surgery system 100 to which the CCU 139-1 belongs. In this case, the control device 401 may belong to the endoscopic surgery system 100 to which the CCU 139-1 belongs to, or to the endoscopic surgery system 100 to which the CCU 139-2 belongs to, or may not belong to those endoscopic surgery systems 100. For example, the control device 401 may be configured as a device that controls those endoscopic surgery systems 100.

Furthermore, the control device 401 may be installed at a place, such as a central management center, where the endoscopic surgery system 100 is not placed. In such a case, the endoscopic surgery system 100 to which the CCU 139-1 belongs and the endoscopic surgery system 100 to which the CCU 139-2 belongs may be installed in an identical surgery room, in different surgery rooms, or in different hospital wards or hospitals.

It should be noted that the number of CCUs 139 to be resources is arbitrary as long as it is multiple. Further, the number of arithmetic processing sections of each CCU 139 may be unified or not unified.

Control Device

Figure 10:
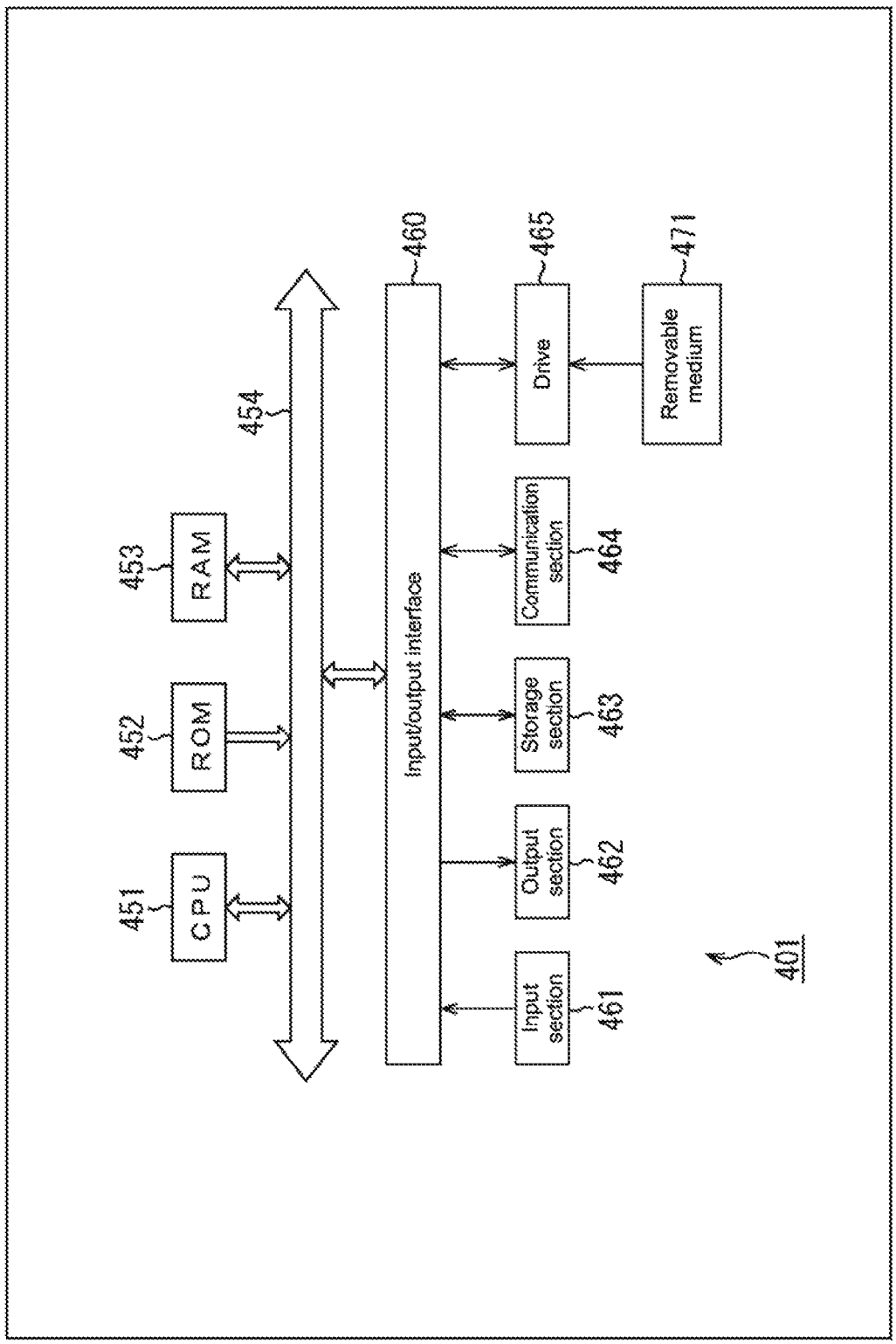
FIG. 10 is a block diagram of a main configuration example of a control device.

FIG. 10 is a block diagram of a main configuration example of the control device 401. As illustrated in FIG. 10, the control device 401 includes a central processing unit (CPU) 451, a read only memory (ROM) 452, a random access memory (RAM) 453, a bus 454, an input/output interface 460, an input section 461, an output section 462, a storage section 463, a communication section 464, and a drive 465.

The CPU 451, the ROM 452, and the RAM 453 are connected to one another via the bus 454. The input/output interface 460 is also connected to the bus 454. To the input/output interface 460, the input section 461 to the drive 465 are connected.

For example, the input section 461 includes arbitrary input devices such as a keyboard, a mouse, a touch panel, an image sensor, a microphone, a switch, an input terminal. For example, the output section 462 includes arbitrary output devices such as a display, a speaker, and an output terminal. The storage section 463 includes arbitrary storage media such as a hard disk, a RAM disk, and a nonvolatile memory such as solid state drive (SSD) and universal serial bus (USB) (registered trademark) memories. The communication section 464 includes a wired or wireless communication interface or both of the communication interfaces of arbitrary communication standards, e.g., Ethernet (registered trademark), Bluetooth (registered trademark), USB, HDMI (High-Definition Multimedia Interface) (registered trademark), and IrDA. The drive 465 drives a removable medium 471 including an arbitrary storage medium such as a magnetic disk, an optical disc, a magneto-optical disk, or a semiconductor memory.

The CPU 451 loads a program or the like stored in, for example, the ROM 452 or the storage section 463 to the RAM 453 and executes the program or the like, to perform processing. The RAM 453 also appropriately stores data or the like necessary for the CPU 451 to execute various types of processing.

Functional Block

Figure 11:
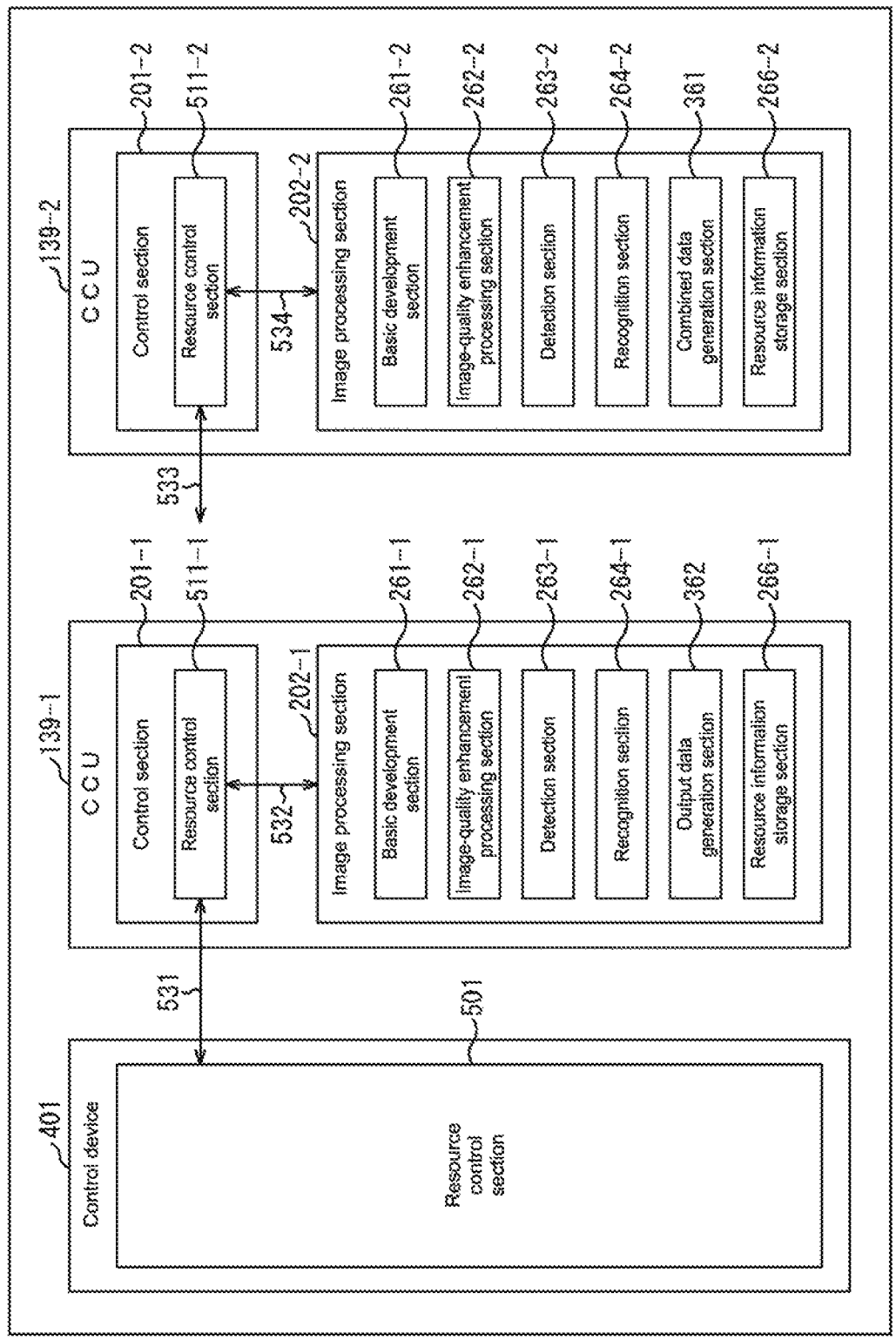
FIG. 11 is a functional block diagram for describing an example of a function achieved by the CCU system.

The functions achieved by the above-mentioned hardware resources will be described. FIG. 11 illustrates an example of a functional block of functions achieved by the control device 401, the control section 201-1 (a first camera controller) and the image processing section 202-1 of the CCU 139-1, and the control section 201-2 (a second camera controller) and the image processing section 202-2 of the CCU 139-2. As illustrated in FIG. 11, the control device 401 achieves a resource control section 501. The control section 201-1 achieves a resource control section 511-1. The control section 201-2 achieves a resource control section 511-2. The image processing section 202-1 and the image processing section 202-2 achieve a functional block similar to that of the second embodiment (FIG. 7).

The resource control section 501 performs, for example, processing distribution to the resource control section 511-1 and the resource control section 511-2 (arrow 531 and arrow 533). The resource control section 511-1 performs, for example, processing distribution to the resources of the image processing section 202-1 (arrow 532). The resource control section 511-2 performs, for example, processing distribution to the resources of the image processing section 202-2 (arrow 534).

This allows the resource control section 501 to perform the processing by using the plurality of resources as in the case of the first embodiment, thus improving the utilization efficiency of the resources.

Flow of Image Processing

Next, an example of a flow of the image processing in this case will be described with reference to a flowchart of FIGS. 12 and 13.

Figure 12:
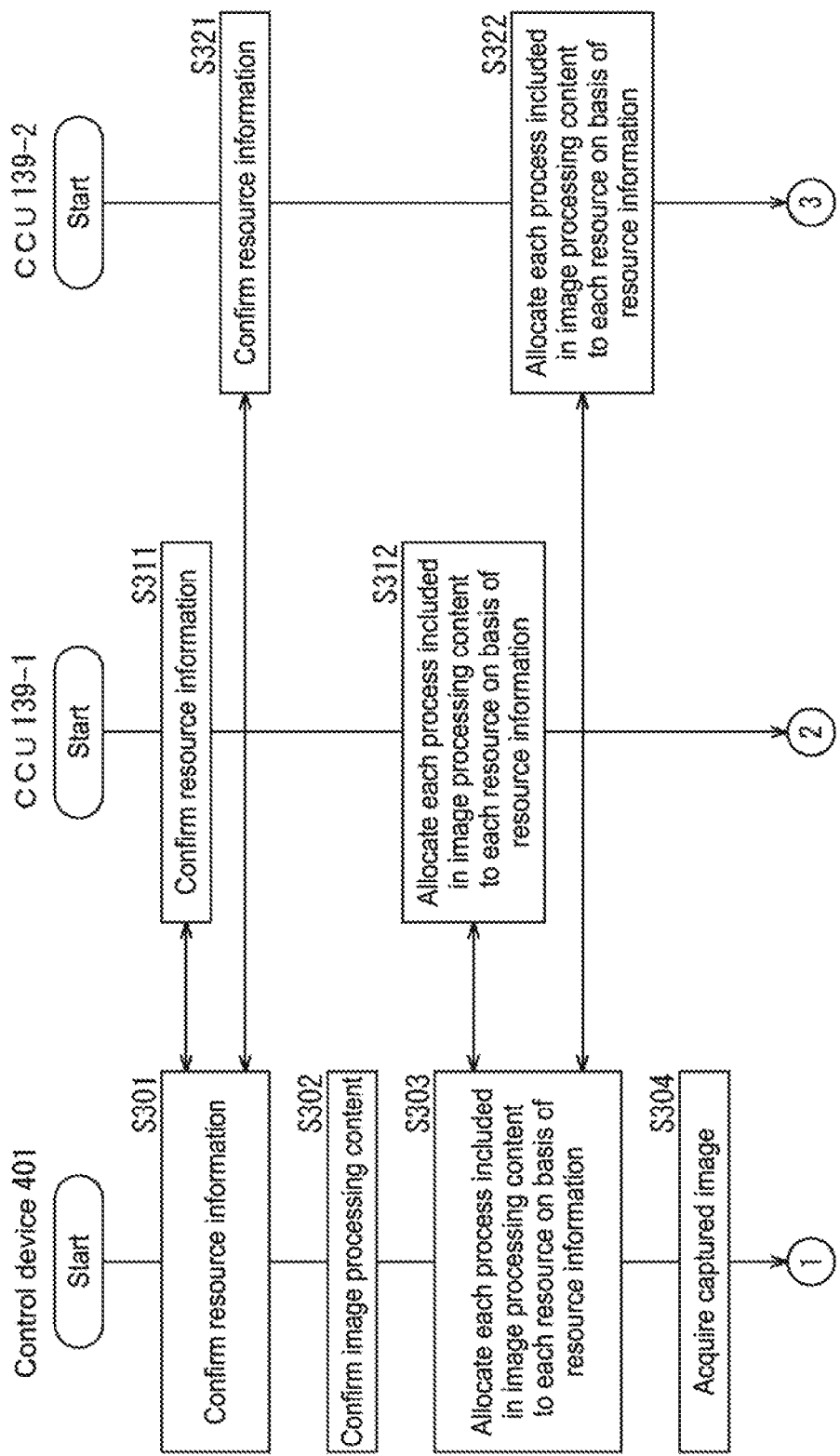
FIG. 12 is a flowchart for describing an example of a flow of image processing.

When the image processing is started, the resource control section 501 of the control device 401, the resource control section 511-1 of the CCU 139-1, and the resource control section 511-2 of the CCU 139-2 perform processing in cooperation with one another and confirm resource information (Step S301, Step S311, and Step S321 of FIG. 12).

More specifically, the resource control section 511-1 reads resource information of the image processing section 202-1 from the resource information storage section 266-1, holds the resource information, and supplies it to the resource control section 501. Similarly, the resource control section 511-2 reads resource information of the image processing section 202-2 from the resource information storage section 266-2, holds the resource information, and supplies it to the resource control section 501.

In Step S302, the resource control section 501 confirms image processing content. In Step S303, the resource control section 501 then allocates each process included in the image processing content to each of the resources (the image processing section 202-1 or the image processing section 202-2) on the basis of the resource information of the image processing section 202-1 and the resource information of the image processing section 202-2.

In Step S312, the resource control section 511-1 cooperates with the processing of Step S303 to allocate each process included in the image processing content, which is allocated to the image processing section 202-1, to each of the resources of the image processing section 202-1 on the basis of the resource information of the image processing section 202-1.

Similarly, in Step S322, the resource control section 511-2 cooperates with the processing of Step S303 to allocate each process included in the image processing content, which is allocated to the image processing section 202-2, to each of the resources of the image processing section 202-2 on the basis of the resource information of the image processing section 202-2.

In Step S304, the resource control section 501 acquires data such as captured images (raw data of endoscopic image) via the communication section 464, the data being supplied from the endoscope 101.

Figure 13:
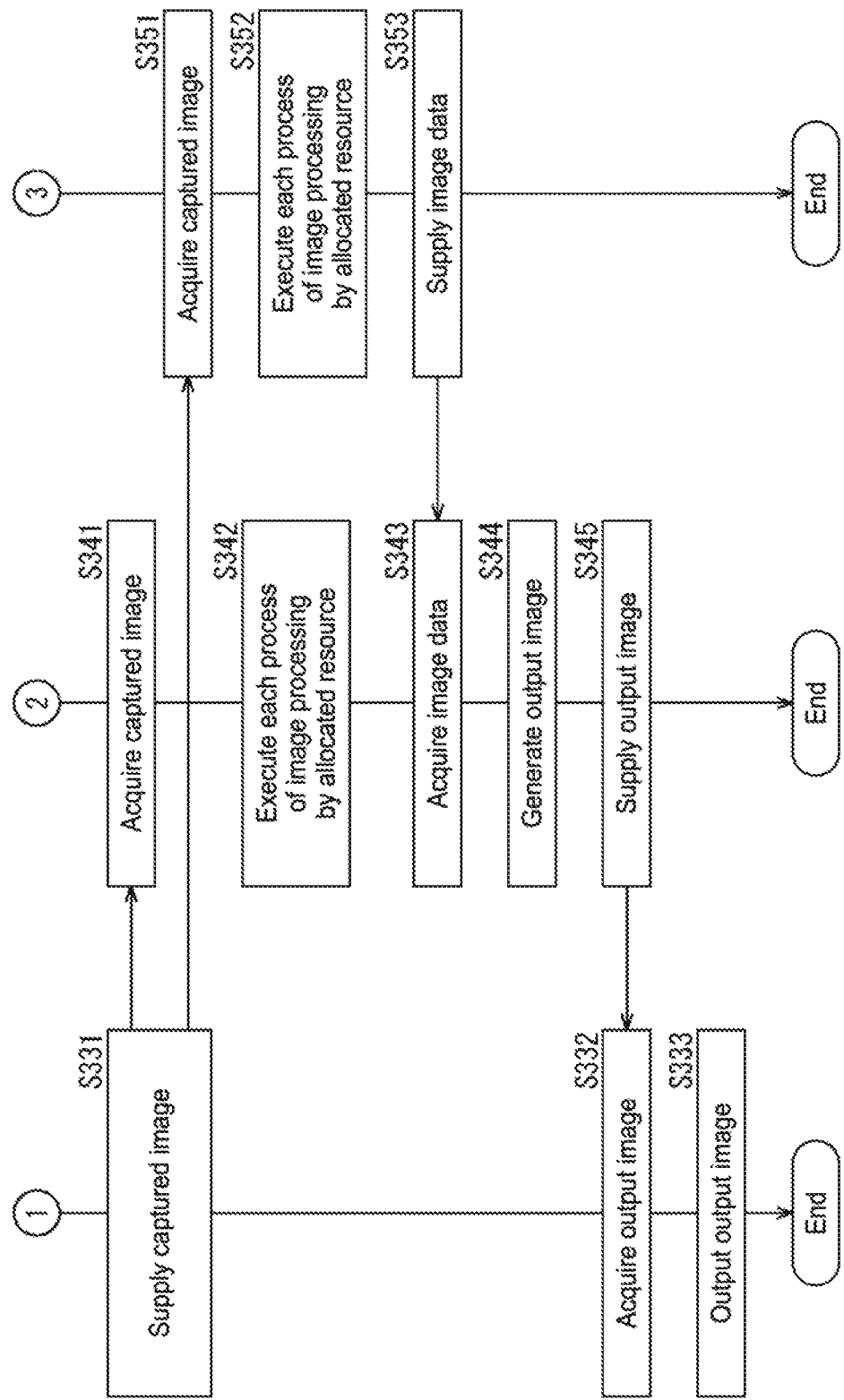
FIG. 13 is a flowchart following FIG. 12 for describing the example of the flow of the image processing.

In Step S331 of FIG. 13, the resource control section 501 supplies the data such as captured images to the resource control section 511-1 and the resource control section 511-2. In Step S341, the resource control section 511-1 acquires the data such as captured images. Further, in Step S351, the resource control section 511-2 acquires the data such as captured images.

In Step S342, the resource control section 511-1 causes the allocated resources of the image processing section 202-1 to execute respective processes of the image processing. Under the control of the resource control section 511-1, each functional block of the image processing section 202-1 performs respective processes by using the allocated resources.

In Step S352, the resource control section 511-2 causes the allocated resources of the image processing section 202-2 to execute respective processes of the image processing. Under the control of the resource control section 511-2, each functional block of the image processing section 202-2 performs respective processes by using the allocated resources.

In Step S353, the resource control section 511-2 supplies the combined data to the CCU 139-1, the combined data being generated in the combined data generation section 361. In Step S343, the resource control section 511-1 acquires the combined data.

In Step S344, the resource control section 511-1 controls the output data generation section 362 to generate output data. The output data generation section 362 generates output data by using a processing result of Step S342 and the combined data acquired in Step S343 and supplies the output data to the resource control section 511-1.

In Step S345, the resource control section 511-1 supplies the output data to the resource control section 501. In Step S333, the resource control section 501 outputs the output data to the outside of the control device 401.

When the image processing is performed as described above, the processing regarding instant output of medical data can be adaptively distributed to the plurality of arithmetic processing sections, thus improving the utilization efficiency of the resources. For example, a high-quality endoscopic image, which is difficult to achieve by the single CCU 139, can be provided to the surgeon. This allows the surgeon to improve the efficiency of the surgery procedure. Further, since the arithmetic resources can be adaptively distributed as described above, it becomes unnecessary to provide the single CCU 139 with high arithmetic performance. This can provide a highly functional service to the user at low device costs.

5. Fourth Embodiment

CCU System

It should be noted that, in the CCU system described in the second embodiment, for example, the external resource is not limited to the CCU 139 and may be any device. For example, as illustrated in FIG. 14, a configuration of cloud computing in which a plurality of apparatuses share one function and cooperate to perform processing via a network can be provided.

Figure 14:
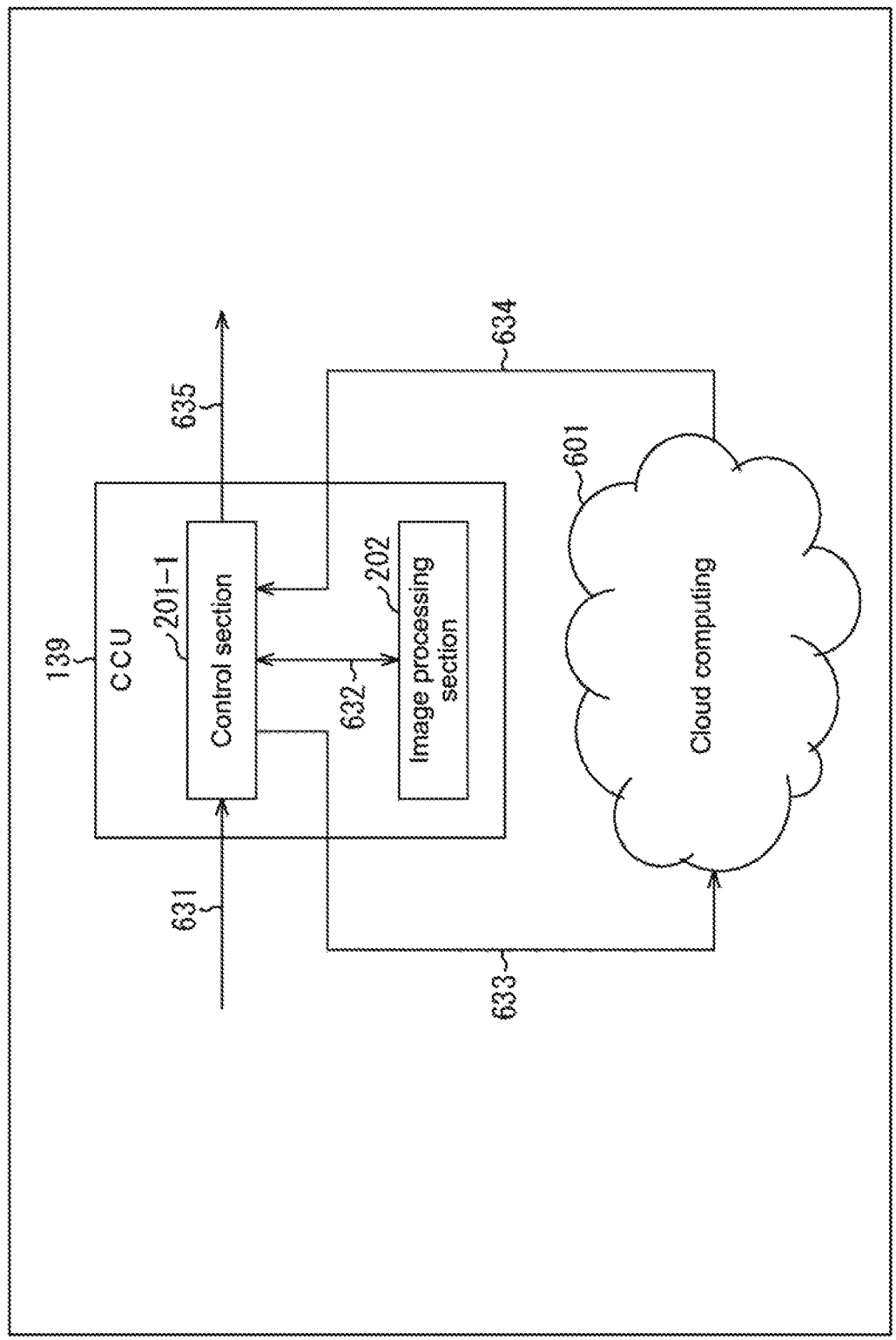
FIG. 14 is a functional block diagram for describing an example of a function achieved by the CCU system.

In a CCU system illustrated in FIG. 14, unlike the case of FIG. 6, the external resource is configured by cloud computing 601. In other words, the external resource has an arbitrary configuration. It should be noted that the cloud computing 601 is, for example, a server group including a plurality of server apparatuses each including a CPU, a RAM, a ROM, a GPU, an HDD, and an SDD.

In this case as well, as in the case of the second embodiment, a CCU 139 is used as a main resource, and a control section 201 thereof controls an image processing section 202 and the cloud computing 601. Therefore, the configuration and the content of processing are similar to those of the second embodiment, and description thereof will thus be omitted.

For example, an image signal or the like transmitted from the endoscope 101 is supplied to the control section 201 of the CCU 139 (via a communication section 224) (arrow 631). The control section 201 distributes processing to the image processing section 202 and the cloud computing 601 as an external resource on the basis of processing content and resource information of them (arrow 632 and arrow 633). The image processing section 202 and the cloud computing 601 each execute processing allocated thereto. The cloud computing 601 supplies a processing result to the image processing section 202 via the control section 201 (arrow 634 and arrow 632). The image processing section 202 combines a processing result thereof and the processing result of the cloud computing 601, generates output data, and outputs the output data to, for example, the display device 141 via the control section 201 (arrow 632 and arrow 635). On the display device 141, an endoscopic image or the like included in that output data is displayed.

When the image processing is performed as described above, the processing regarding instant output of medical data can be adaptively distributed to the plurality of arithmetic processing sections, thus improving the utilization efficiency of the resources. This allows achievement of the processing exceeding the arithmetic processing performance of the internal resources by distributing the processing to the external resource. For example, a high-quality endoscopic image, which is difficult to achieve by the arithmetic processing sections of the internal resources, can be provided to the surgeon. This allows the surgeon to improve the efficiency of the surgery procedure.

At that time, the control section 201 may refer to the availability of occupancy, as resource information of the external resource, and determine whether the external resource is available or not. Further, when determining that the external resource is available, the control section 201 may present, to the surgeon, options on whether to perform high-performance processing or not, and may adaptively distribute the processing to the external resource according to the option selected by the surgeon. This can provide to the surgeon an endoscopic image with which the surgery procedure of the surgeon is improved, depending on the status of the external resource.

Further, the control section 201 may refer to a usage fee generated when the external resource is used, as resource information of the external resource. In consideration of the usage fee and the user's set budget, the control section 201 may present to the surgeon an available time for the external resource and options on whether to perform high-performance processing or not, and then adaptively distribute the processing to the external resource according to the option selected by the surgeon. This can provide to the surgeon an endoscopic image with which the surgery procedure of the surgeon is improved, depending on the budget. It should be noted that the resource information of the external resource may be performance of the arithmetic processing, consumed power, a response speed, a cumulative operating time, or a hardware version.

Further, the control section 201 may determine whether the processing content needs to be processed at a high response speed, and may adaptively distribute the processing such that the processing that needs quick response processing uses the internal resources and that the processing that does not need quick response processing uses the external resource. The processing that needs quick response processing is, for example, real-time image-quality enhancement processing or real-time lesion detection performed on an endoscopic image. The processing that does not need quick response processing is, for example, monitoring of bleeding/burn injury out of the field of view, an automatic diagnosis of a pit pattern (pattern of a recess of large intestine mucous membrane surface), recording and analysis of the progress status of surgery, imparting of a tag indicating a surgery scene where the image is acquired, calculation of tissue deformation, search for associated images on a real-time image, comparison between images in diagnosis and in surgery, delay/quality/volume adjustment of sound recording, quality enhancement/blur correction of recorded images, metarecording/metareproduction of a vital status, and bleeding-site estimation processing. It should be noted that determination of the processing content by the control section 201 may be performed by using a table stored in advance, or may be selected by the user.

Using the cloud computing described above, even when a situation that is not assumed from preoperative information occurs during surgery, and the situation needs processing that needs resources more than the internal resources thereof, the external resource can be adaptively used to perform the processing. For example, even when the use of only the image-quality enhancement processing is scheduled before surgery, due to sudden bleeding, blood-vessel highlighting processing and bleeding-site estimation processing are used in combination in some cases. In such a case, if the control section distributes the image-quality enhancement processing and the blood-vessel highlighting processing to the internal resources, and distributes the bleeding-site estimation processing to the external resource, it is also possible to cope with a case where the internal resources fail to perform the processing.

6. Others

Software

The series of processing described above can be executed by hardware or can be executed by software. Further, part of the processing can be executed by hardware and the other processing can be executed by software. In a case where the series of processing described above is executed by software, programs or the like constituting the software are installed from a network or a recording medium.

For example, in the case of the CCU 139 of FIG. 2, the recording medium is configured separately from the device main body by the removable medium 231 in which a program or the like is recorded, the program being distributed in order to deliver the program or the like to a user. In such a case, for example, the removable medium 231 is mounted to the drive 225 to cause the drive 225 to read the program or the like stored in the removable medium 231 and cause the storage section 223 to install the program or the like therein.

Further, this program can also be provided via a wireless or wired transmission medium such as a local area network, the Internet, and digital satellite broadcasting. For example, in the case of the CCU 139 of FIG. 2, the program can be received in the communication section 224 and installed in the storage section 223.

In addition, this program can also be previously installed in the storage unit, the ROM, or the like. For example, in the case of the CCU 139 of FIG. 2, the program can also be previously installed in the built-in ROM or the like of the storage section 223 or the control section 201.

User Interface

Figure 15:
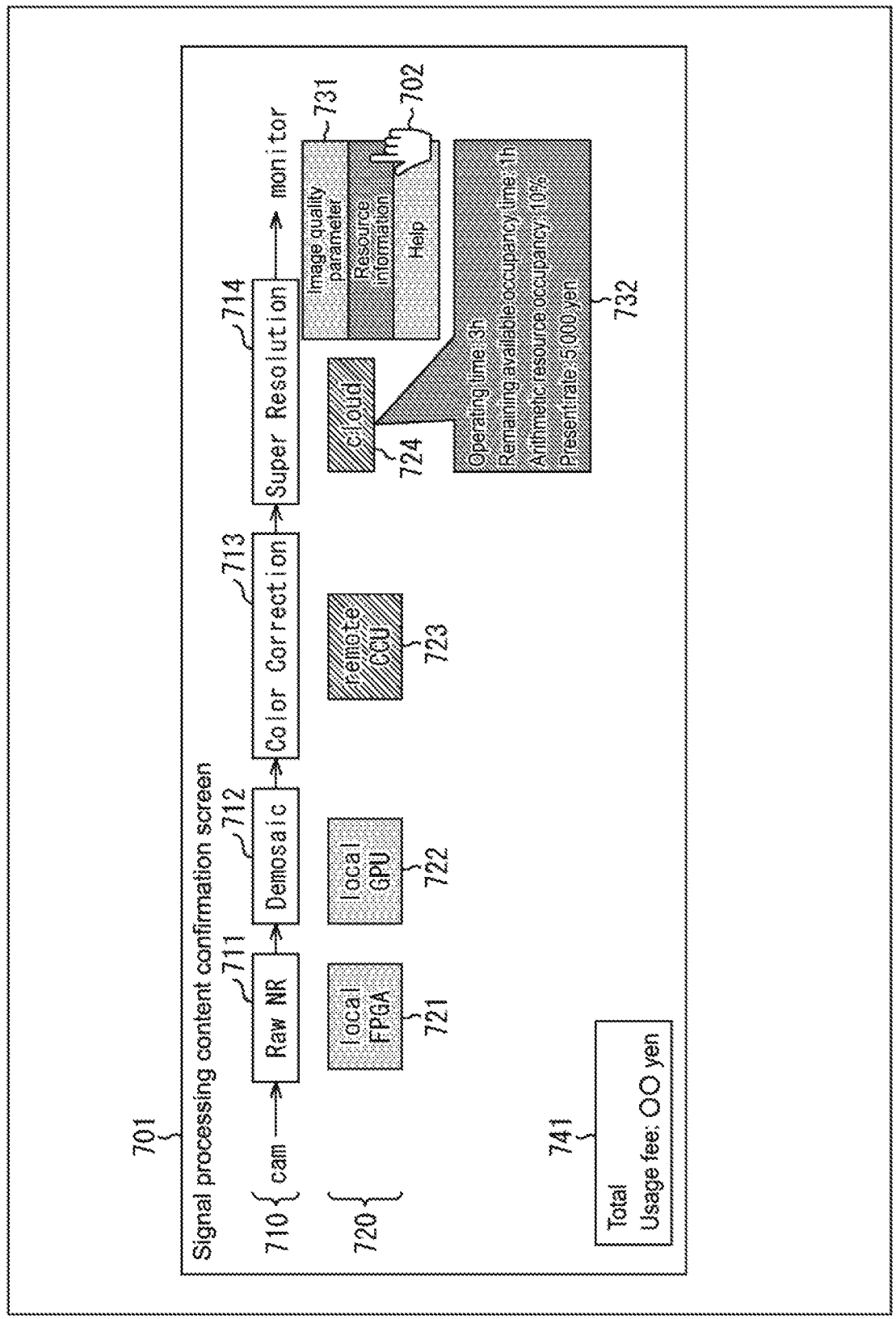
FIG. 15 is a diagram for describing an example of a user interface.

In each of the embodiments described above, a user interface (UI) of the resource distribution processing may be displayed as in FIG. 15, for example.

A signal processing content confirmation screen 701 illustrated in FIG. 15 is a UI for a user to confirm content of signal processing to be executed, information regarding a resource allocated to corresponding signal processing, or the like.

As illustrated in FIG. 15, a list 710 of signal processing to be executed is displayed on the upper part of the signal processing content confirmation screen 701. For example, in the case of the signal processing content confirmation screen 701 of FIG. 15, a "Raw NR" icon 711, a "Demosaic" icon 712, a "Color Correction" icon 713, and a "Super Resolution" icon 714 are displayed between "cam" and "monitor". The "Raw NR" icon 711 indicates noise reduction processing for a raw image. The "Demosaic" icon 712 indicates demosaic processing. The "ColorCorrection" icon 713 indicates color correction processing. The "Super Resolution" icon 714 indicates super-resolution processing. In other words, the list 710 indicates that noise reduction processing (Raw NR), demosaic processing (Demosaic), color correction processing (Color Correction), and super-resolution processing (Super Resolution) for a raw image are performed between imaging (cam) and image display (monitor).

Further, below the list 710, a list 720 of resources, to which each signal processing of the list 710 is allocated, is displayed. For example, in the case of the signal processing content confirmation screen 701 of FIG. 15, the list 720 displays a "local FPGA" icon 721 below the "Raw NR" icon 711, a "local GPU" icon 722 below the "Demosaic" icon 712, a "remote CCU" icon 723 below the "Color Correction" icon 713, and a "cloud" icon 724 below the "Super Resolution" icon 714.

The "local FPGA" icon 721 is processing indicating that a local FPGA (the CCU) is a resource. In other words, in the list 720, the "local FPGA" icon 721 is disposed below the "Raw NR" icon 711, which indicates that the FPGA of the CCU is allocated, as a resource, to the noise reduction processing for a raw image.

The "local GPU" icon 722 is processing indicating that a local GPU (the CCU) is a resource. In other words, in the list 720, the "local GPU" icon 722 is disposed below the "Demosaic" icon 712, which indicates that the GPU of the CCU is allocated, as a resource, to the demosaic processing.

The "remote CCU" icon 723 is processing indicating that a remote CCU (another CCU that may be an external resource) is a resource. In other words, in the list 720, the "remote CCU" icon 723 is disposed below the Color Correction" icon 713, which indicates that the remote CCU is allocated, as a resource, to the color correction processing.

The "cloud" icon 724 is processing indicating that cloud computing is a resource. In other words, in the list 720, the "cloud" icon 724 is disposed below the "Super Resolution" icon 714, which indicates that the cloud computing is allocated, as a resource, to the super-resolution processing.

As described above, the processing content to be executed and a resource allocated to each process are displayed so as to indicate a correspondence relationship therebetween. In other words, this signal processing content confirmation screen 701 indicates the allocated arithmetic processing sections (resources), for each process to be executed as processing regarding instant output of medical data. Therefore, the user can easily grasp those pieces of information (with which resource each process is performed).

It should be noted that the icons of the list 720 may be displayed such that the types of resources or the like are distinguishable (i.e., the display method is changed). For example, the local resource (the CCU) and a resource of the external resource (another CCU, cloud computing, etc.) may be displayed so as to be distinguishable (i.e., distinguishable on whether the resource is an external resource or not). A distinguishable display method (display method that is changed according to the type of resources) is arbitrarily set. For example, at least one of the color, density, brightness, size, thickness, line type, and shape of the icons (or characters displayed on icons) may be changed. For example, in the case of FIG. 15, the "local FPGA" icon 721 and the "local GPU" icon 722 corresponding to the local resources are displayed as gray icons, and the "remote CCU" icon 723 and the "cloud" icon 724 corresponding to the external resource are displayed as hatched icons. When the display is changed in such a manner, the user can intuitively grasp the types of resources corresponding to the respective icons, or the like.

Further, by specifying each icon of the list 720, information regarding the processing corresponding to that icon may be obtained. For example, in the example of FIG. 15, when the user operates a cursor 702 to specify the "cloud" icon 724, a menu screen 731 is displayed. In this menu screen 731, a list of processing selectable by the user is displayed. For example, in the case of FIG. 15, the menu screen 731 displays menus of "image quality parameter", "resource information", "help", and the like.

The "image quality parameter" menu is a menu to display information regarding an image quality parameter. The "resource information" menu is a menu to display information regarding the resources. The "help" menu is a menu to display help information regarding description or operation of content displayed on the screen. For example, when the user operates the cursor 702 to select the "resource information" menu, as in the example of FIG. 15, a pop-up 732 is displayed. The pop-up 732 displays information regarding cloud computing allocated to super-resolution processing, such as "operating time", "remaining available occupancy time", "arithmetic resource occupancy", "present rate", and the like.

The "operating time" is information indicating an operating time of the resource up to the present time. The example of FIG. 15 indicates that the operating time of the cloud computing is 3 hours (3 h). The "remaining available occupancy time" is information indicating a remaining time in which the resource can be occupied. For example, a time obtained by subtracting the above-mentioned operating time from a time length reserved for occupancy is displayed as the remaining available occupancy time. The example of FIG. 15 indicates that the remaining time for which the cloud computing can be occupied is 1 hour (1 h). The "arithmetic resource occupancy" is information indicating a proportion (rate) at which the resource is occupied actually. In other words, the "arithmetic resource occupancy" is information indicating to what extent the resource has free space (room). The example of FIG. 15 indicates that the occupancy of the cloud computing is 10%. The "present rate" is information indicating the usage fee up to the present time for a usage status of the resources. The example of FIG. 15 indicates that the usage fee of the cloud computing is five thousand yen (5,000 yen).

In such a manner, the user can more easily grasp various types of information for respective resources.

It should be noted that the signal processing content confirmation screen 701 displays the total usage fee ("total usage fee") on the lower left thereof. Therefore, the user can easily grasp the expense up to the present time.

The signal processing content confirmation screen 701 has an arbitrary configuration and is not limited to the example of FIG. 15. For example, different information may also be displayed on the signal processing content confirmation screen 701. For example, as illustrated in FIG. 16, the use rate of each resource, the setting of a frame for a region that is subjected to the image-quality enhancement processing, and the like may also be displayed.

Figure 16:
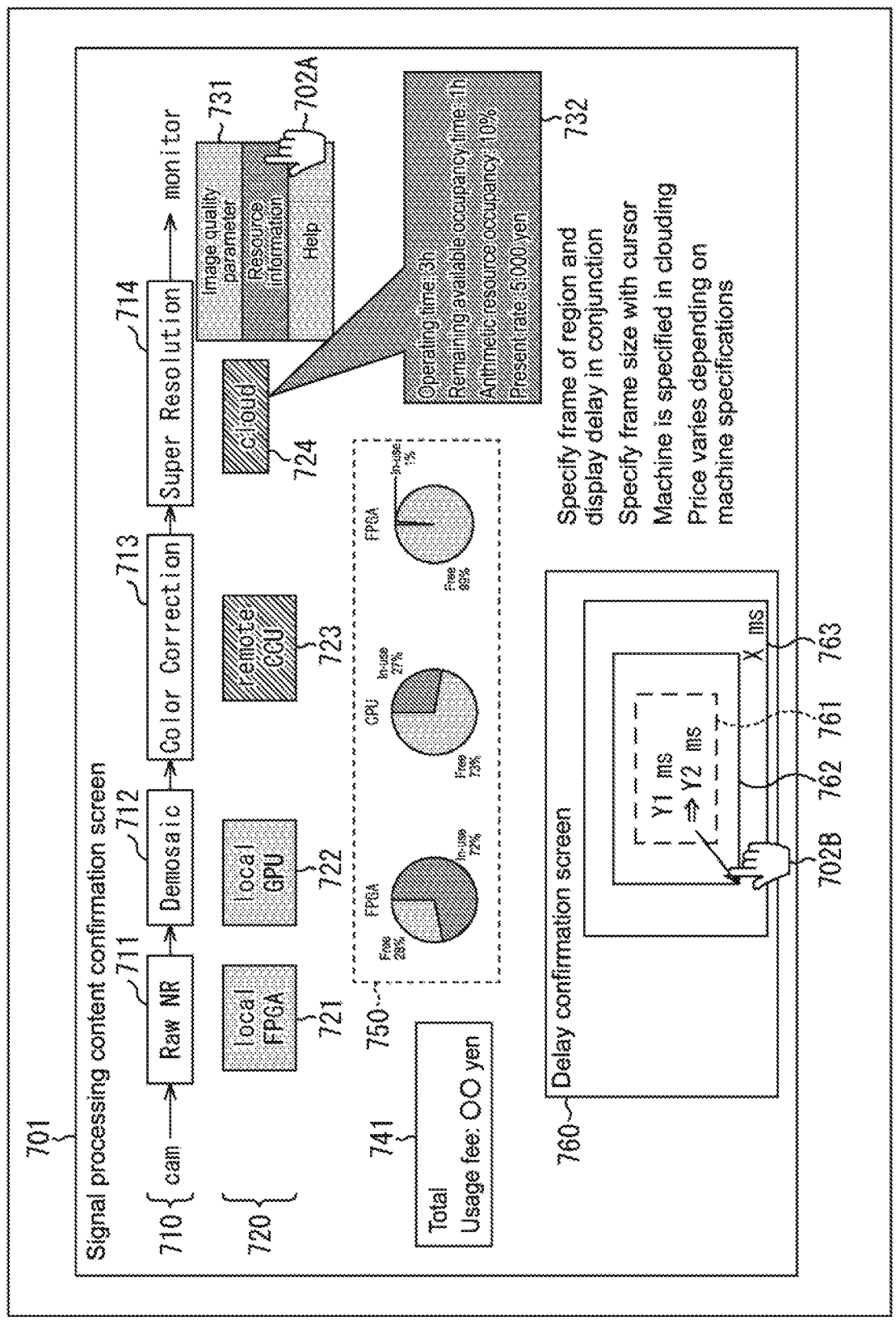
FIG. 16 is a diagram for describing an example of a user interface.

In the example of FIG. 16, the use rate of each resource is displayed as a pie chart in a region 750 below the list 720 of the signal processing content confirmation screen 701. Such a display allows the user to intuitively grasp the use rate of each resource.

Further, in the example of FIG. 16, a delay confirmation screen 760 is displayed below the signal processing content confirmation screen 701. The delay confirmation screen 760 is a UI on which the user performs setting or confirmation regarding delay of a region of interest (region whose image quality is enhanced) of a medical image, the medical image being presented to the surgeon (displayed for the surgeon).

In the delay confirmation screen 760, for example, the user can perform, by operating the cursor 702, setting of a display method (number of frames, color, thickness, shape, etc.) for a frame of a region of interest in a case where delay is caused due to the image-quality enhancement processing. Further, for example, the user can specify, by operating the cursor 702, the size, shape, and the like of the region of interest. In such a case, the amount of delay due to the image-quality enhancement processing, which corresponds to the set size, shape, and the like of the region of interest, may be displayed. Providing such a delay confirmation screen 760 allows the user to perform setting or confirmation regarding delay of a region of interest of a medical image.

Figure 17:
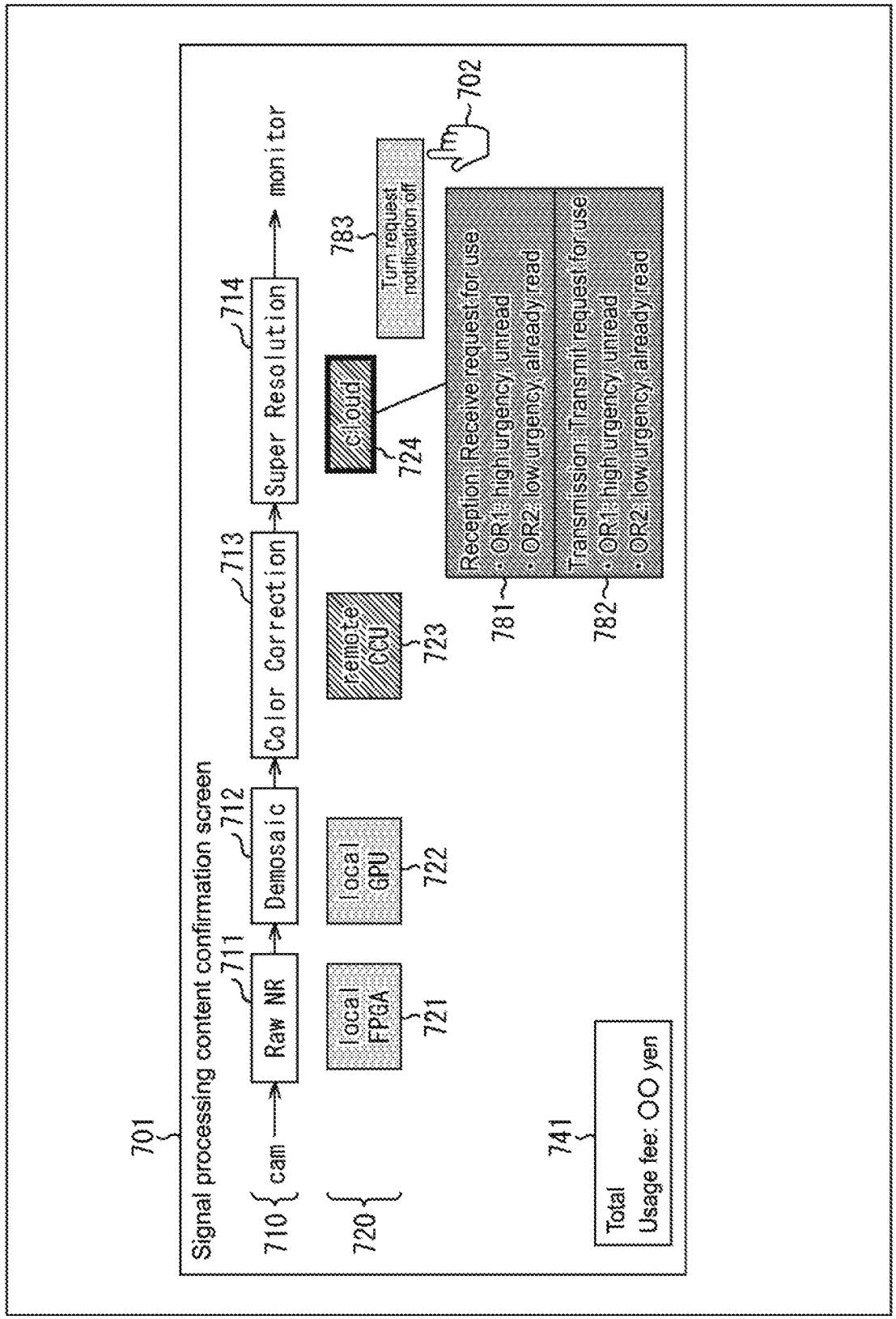
FIG. 17 is a diagram for describing an example of a user interface.

Further, for example, as illustrated in FIG. 17, in this signal processing content confirmation screen 701, communication between users (operators) for a demand or the like regarding use of the resources may be performed. For example, a user may transmit a request of the release of a resource occupied by another user (and exclusive use of the resource by the user) may be requested to the other user. Further, the user may receive from another user a request of the release of a resource occupied by the user (and exclusive use of the resource by the other user). As a matter of course, the user may perform both of the requests.

In the case of FIG. 17, for example, when the user operates the "cloud" icon 724 of the signal processing content confirmation screen 701 with the cursor 702, a request reception confirmation screen 781, a request transmission confirmation screen 782, and a request notification termination icon 783 are displayed.

The request reception confirmation screen 781 is a UI for the user to confirm a reception status of a request transmitted to the user from another user. The example of FIG. 17 indicates that the user receives a request transmitted from another user (OR2) for a resource (cloud) occupied by the user, the request having low urgency, and the request is already confirmed (already read). Further, the example of FIG. 17 indicates that the user receives a request from another user (OR1), the request having high urgency, and the request is not yet confirmed (unread). Such display allows the user to easily grasp the reception status of the requests.

The request transmission confirmation screen 782 is a UI for the user to confirm a transmission status of a request transmitted by the user to another user. The example of FIG. 17 indicates that the user transmits a request for a resource occupied by another user (OR2), the request having low urgency, and the request is already confirmed (already read) by the user (OR2). Further, the example of FIG. 17 indicates that the user transmits a request for a resource occupied by another user (OR1), the request having high urgency, and the request is not yet confirmed (unread) by the user (OR1). Such display allows the user to easily grasp the transmission status of the requests.

The request notification termination icon 783 is a UI to terminate displaying of the request reception confirmation screen 781 and the request transmission confirmation screen 782. For example, when the user operates the request notification termination icon 783 with the cursor 702, displaying of the request reception confirmation screen 781 and the request transmission confirmation screen 782 is terminated (the request reception confirmation screen 781 and the request transmission confirmation screen 782 are deleted). In such a case, the request notification termination icon 783 may also be deleted. Displaying those icons allows the user to terminate displaying of the request reception confirmation screen 781 and the request transmission confirmation screen 782 more easily.

Further, when the user allocates the resources (particularly, external resource), a list of available resources may be presented as a UI. A resource selection screen 791 illustrated in FIG. 18 is a UI for the user to select a resource allocated to the processing to be executed. As illustrated in FIG. 18, the resource selection screen 791 includes a list of available external resources. The user selects a desired resource from the list by use of the cursor 792, to thus easily select a resource allocated to the processing.

It should be noted that this list includes not only a resource name (machine name) but also information regarding a resource, such as a reservation status, an operation status, a rate, an available time, selectable processing, and the like of the resource. Therefore, the user can select the optimal resource (the most advantageous resource) for the processing to be executed, on the basis of those pieces of information.

Further, the user may reserve a plurality of resources on the resource selection screen 791. For example, as illustrated in FIG. 18, two resources may be reserved as a primary reservation and a secondary reservation. In this case, the resource primarily reserved is preferentially used, and if the resource primarily reserved becomes unavailable due to unforeseeable circumstances, the resource secondarily reserved is allocated to the processing. For example, when the period for the resource primarily reserved expires because the surgery is prolonged, for example, the resource primarily reserved is switched to the resource secondarily reserved. In a medical field, an unexpected situation may occur. Thus, ensuring a plurality of resources in such a manner can achieve safer medical support.

Supplementary Note

The embodiments of the present technology are not limited to the embodiments described above and can be variously modified without departing from the gist of the present technology.

For example, the present technology can be performed as any configuration forming an apparatus or system, e.g., a processor such as a system large scale integration (LSI), a module using a plurality of processors and the like, a unit using a plurality of modules and the like, a set obtained by adding another function thereto (i.e., a part of a configuration of apparatus), or the like.

It should be noted that, in this specification, a system means an aggregation of a plurality of constituent elements (apparatus, module (parts), and the like), regardless of whether all constituent elements are included in the identical casing. Therefore, a plurality of apparatuses housed in separate casings and connected to one another via a network is a system, and one apparatus housing a plurality of modules in one casing is also a system.

Further, for example, the configuration described as one apparatus (or processing unit) may be divided into a plurality of apparatuses (or processing units). Conversely, the configurations described as a plurality of apparatuses (or processing units) may be configured as one apparatus (or processing unit). Further, a configuration other than that described above may be added to each apparatus (or each processing unit) as a matter of course. Furthermore, if a configuration or operation of the entire system is substantially identical, a part of a configuration of a certain apparatus (or processing unit) may be included in a configuration of another apparatus (or another processing unit).

Further, for example, the above-mentioned program can be executed in an arbitrary apparatus. In this case, that apparatus only needs to have a necessary function (functional block or the like) to obtain necessary information.

Further, for example, the steps described in the flowcharts described above can be executed by one apparatus or shared and executed by a plurality of apparatuses. In addition, in a case where one step includes a plurality of processing steps, the plurality of processing steps in the step can be executed by one apparatus or shared and executed by a plurality of apparatuses. In other words, a plurality of processing steps in one step can be executed as processing including a plurality of steps. Conversely, processing described as a plurality of steps can be executed as one step.

In the program executed by a computer, steps describing the program may be processed chronologically along the described order in this specification or may be processed in parallel or at a necessary timing such as when an invocation is performed. In other words, each step may be processed in an order different from the above-mentioned order as long as there is no contradiction. Furthermore, the steps describing the program may be processed in parallel with the processing of another program or may be processed in combination with the processing of another program.

The CPU may be defined as having N1 core(s) and N1*M1 thread(s), where M1=1~3, "core" is processing circuit, and "thread" is a minimum unit of information.

The GPU may be defined as having N2 core(s) and N2*M2 thread(s), where M2=100~ and N2>10*N1 (i.e., GPU has at least more than 10 times the core of CPU). In addition, the GPU may be a dedicated graphics processor efficiently implementing graphics operations, such as 2D, 3D graphics operations and/or digital video related functions. A GPU may include special programmable hardware that performs graphics operations, e.g. blitter functions, polygon/3D rendering, pixel shading, texture mapping, and vertex shading. A GPU may fetch data from a frame buffer and blend pixels together to render an image back into the frame buffer for display. GPUs may also control the frame buffer and permit the frame buffer to be used to refresh a display. A GPU may perform graphics processing tasks in place of CPUs coupled to the GPU to output raster graphics images to display devices through display controllers. While a CPU consists of a few cores optimized for sequential serial processing, a GPU has a parallel architecture consisting of hundreds or more of smaller efficient cores designed for simultaneous handling of multiple tasks thereby performing parallel operations on multiple sets of data.

The FPGA can be defined as a logic circuit, for example, a logic formed by a language dedicated to hardware design standardized by IEEE such as VHDL and Verilog HDL. The FPGA has circuit information, and a content of signal processing for the input signal in FPGA is determined by the circuit information.

The present technology has been described as various embodiments in this specification, and those embodiments can be performed independently as long as there is no contradiction. As a matter of course, the present technology can be performed in combination with arbitrary embodiments. For example, a part or all of the present technology that has been described in any embodiment can also be performed in combination with a part or all of the present technology that has been described in a different embodiment. Further, an arbitrary part or all of the present technology described above can also be performed in combination with a different technology that has not been described above.

It should be noted that the present technology can also have the following configurations.

(1)

A medical image processing apparatus for allocating at least two medical imaging processes to a plurality of assignable processing resources, the plurality of assignable processing resources being allocated by the medical image processing apparatus, the medical image processing apparatus comprising:

circuitry configured to acquire medical image processing content, from medical equipment, to be processed according to the at least two medical imaging processes prior to display on a display device connected to a surgical operating room network, acquire a resource information of the plurality of assignable processing resources, and allocate each of the at least two medical imaging processes to a different one of the plurality of assignable processing resources based on the resource information of the plurality processing resources and the medical image processing content.

(2)

The apparatus of (1), in which a first processor of the plurality of assignable processing resources being a first type of arithmetic processor that is a different type than a second processor of the plurality of assignable processing resources, the first processor including a graphics processing unit (GPU) and the second processor including a field programmable gate array (FPGA).

(3)

The apparatus of (2), in which the circuitry is configured to allocate to the FPGA a first of the at least two medical imaging processes with a parallel computational demand that is higher than a demand from a second of the at least two medical imaging processes.

(4)

The apparatus of (3), in which the circuitry is configured to allocate one of the at least two medical imaging processings to the GPU during standard operations and allocate the one of the at least two medical imaging processings to the FPGA during emergency operations.

(5)

The apparatus of (4), in which the circuitry is configured to allocate a region of interest (ROI) of a captured image to the GPU to perform image-quality enhancement on the ROI, and allocate a non-ROI portion of the captured image to the FPGA to perform basic image processing.

(6)

The apparatus of (4) or (5), in which the circuitry is further configured to display a visual indication on the captured image of a boundary between the ROI and the non-ROI portion of the captured image.

(7)

The apparatus of (6), in which the circuitry is configured to change an appearance of the visual indication to an indication of at least one of an actuation of a diagnosis support function that supports identification of a lesion by machine learning, and an expense incurred by employing an external processing resource.

(8)

The apparatus of (7), in which the change of appearance is displayed as at least a change of one of color, line thickness, line type, blink duration, transmittance, or brightness.

(9)

The apparatus of any of (1) to (8), in which the resource information includes at least one of arithmetic performance, consumed power, response speed, availability of occupancy, cumulative operating time, hardware version, or usage fee.

(10)

The apparatus of any of (1) to (9), in which the circuitry is configured to change the allocation of the at least two medical imaging processes between the plurality of assignable processing resources based on the medical imaging processing content that includes a high temporal frequency region and a low temporal frequency region, the low temporal frequency region has a lower graphics processing demand than the high temporal frequency region.

(11)

The apparatus of any of (1) to (10), includes the at least two medical imaging processes include surgical assistance processing that includes at least one of highlighting a lesion site on an image, and displaying, as a superposition on the image, a cut part of the lesion site.

(12)

The apparatus of any of (1) to (11), further including a wearable computer that is configured to receive, detect, and process, as an input instruction, a user gesture, the wearable computer being at least one of a glasses-type wearable computer or a head mounted display.

(13)

The apparatus of any of (1) to (12), in which the medical image processing content is acquired from a camera mounted on a multi-joint, multi-link surgical assistance support arm device that is driven by a plurality of actuators.

(14)

The apparatus of any of (1) to (13), in which the circuitry comprises a first camera controller and a second camera controller, in which the first camera controller includes at least one of the plurality of assignable processing resources, and the second camera controller includes at least another of the plurality of assignable processing resources, the first camera controller being configured to allocate a first of the at least two medical imaging processes to the at least one of the plurality of assignable processing resources included in the first camera controller, and allocate a second of the at least two medical imaging processes to the at least another of the plurality of assignable processing resources that is included in the second camera controller.

(15)

The apparatus of any of (1) to (14), in which the circuitry comprises a controller, a first camera controller and a second camera controller, in which the first camera controller includes at least one of the plurality of assignable processing resources, and the second camera controller includes at least another of the plurality of assignable processing resources, the controller includes circuitry configured to allocate a first of the at least two medical imaging processes to the at least one of the plurality of assignable processing resources included in the first camera controller, and allocate a second of the at least two medical imaging processes to the at least another of the plurality of assignable processing resources that is included in the second camera controller.

(16)

The apparatus of any of (1) to (15), in which the circuitry comprises a camera controller that includes at least one of the plurality of assignable processing resources, the circuitry being configured to allocate a first of the at least two medical imaging processes to the at least one of the plurality of assignable processing resources included in the camera controller, and allocate a second of the at least two medical imaging processes to the at least another of the plurality of assignable processing resources that is hosted external to the apparatus, the at least another of the plurality of assignable processing resources is a cloud computing resource.

(17)

The apparatus of (16), in which the circuitry is further configured to display signal processing content confirmation information on a display, in which indications of the at least two medical imaging processes are displayed in association with a first of the plurality of the assignable resources and a second of the plurality assignable resources so as to provide a visual indication of which of the at least two medical imaging processes are assigned to which of the plurality of the assignable resources.

(18)

The apparatus of (17), in which the circuitry is configured to display user-selectable control features that include at least one of a frame size and/or shape of a region of interest (ROI), a resource allocation indication, a usage fee, an occupancy allocation, and an operation time of using a fee-for-use cloud processing resource.

(19)

A medical image processing method, executed in a medical image processing apparatus, for allocating at least two medical imaging processes to a plurality of assignable processing resources, the plurality of assignable processing resources being allocated by the medical image processing apparatus, the medical image processing method including:

acquiring with the circuitry medical image processing content, from medical equipment, to be processed according to the at least two medical imaging processes prior to display on a display device connected to a surgical operating room network; and acquiring a resource information of the plurality of assignable processing resources; and allocating with the circuitry each of the at least two medical imaging processes to a different one of the plurality of assignable processing resources based on the resource information of the plurality of assignable processing resources and the medical image processing content.

(20)

A computing device including:

a display; and circuitry configured to present on the display first icons representing medical image processes to be performed on medical image content, and second icons representing at least one type of assignable processing resource, the second icons being displayed on the display in association with the first icons to indicate which of the assignable processing resources have been assigned to perform a particular one of the medical image processes, in which allocation of the assignable processing resources are assignable from a menu of user-selectable resource information that lists the assignable processing resources that are available to be assigned to the medical image processes represented by the first icons.

(21)

An information processing apparatus, including a control section configured to adaptively distribute processing regarding instant output of medical data to a plurality of arithmetic processing sections.

(22)

The information processing apparatus according to (21), in which the plurality of arithmetic processing sections have different performance.

(23)

The information processing apparatus according to (22), in which the performance includes at least one of performance of arithmetic processing, consumed power, a response speed, availability of occupancy, a cumulative operating time, a hardware version, and a usage fee.

(24)

The information processing apparatus according to (22) or (23), in which the control section is configured to distribute the processing on the basis of content of the processing and the performance of the arithmetic processing sections.

(25)

The information processing apparatus according to (24), in which the control section is configured to grasp the performance of the arithmetic processing sections on the basis of resource information.

(26)

The information processing apparatus according to (25), further including an acquisition unit configured to acquire the resource information, in which the control section is configured to grasp the performance of the arithmetic processing sections on the basis of the resource information acquired by the acquisition unit.

(27)

The information processing apparatus according to any one of (21) to (26), in which the medical data includes data of a medical image.

(28)

The information processing apparatus according to (27), in which the control section is configured to allocate processing regarding a region of interest of the medical image to one of the arithmetic processing sections, the arithmetic processing section being different from another arithmetic processing section, processing regarding another region being allocated to the other arithmetic processing section.

(29)

The information processing apparatus according to (28), in which the control section is configured to set a region around the tip of forceps in the medical image, as the region of interest.

(30)

The information processing apparatus according to (28), in which the control section is configured to set one of a high spatial frequency region and a low spatial frequency region of the medical image as the region of interest.

(31)

The information processing apparatus according to any one of (28) to (30), in which the control section is configured to allocate image-quality enhancement processing for the region of interest and basic development processing for the other region to different arithmetic processing sections, the image-quality enhancement processing including generating a medical image with a higher quality than a usual image quality, the basic development processing including generating a medical image with the usual image quality.

(32)

The information processing apparatus according to any one of (28) to (30), in which the control section is configured to allocate image-quality enhancement processing for the region of interest and detection processing for the other region to different arithmetic processing sections, the image-quality enhancement processing including generating a medical image with a higher quality than a usual image quality, the detection processing including performing detection of bleeding.

(33)

The information processing apparatus according to any one of (28) to (30), in which the control section is configured to allocate processing of improving distinguishability for the region of interest and basic development processing for the other region to different arithmetic processing sections, the processing of improving distinguishability including highlighting a blood vessel and displaying a blood vessel depth, the basic development processing including generating a medical image with a usual image quality.

(34)

The information processing apparatus according to any one of (28) to (30), in which the control section is configured to allocate processing of improving moving image visibility for the region of interest and basic development processing for the other region to different arithmetic processing sections, the processing of improving moving image visibility including frame interpolation, the basic development processing including generating a medical image with a usual image quality.

(35)

The information processing apparatus according to (27), in which the control section is configured to change allocation of the processing regarding the medical image on a frame or line basis.

(36)

The information processing apparatus according to any one of (27) to (35), in which the control section is configured to superimpose a boundary part on a region of the medical image for display, the region being subjected to different processing content, and the boundary part can be changed on the basis of the processing content.

(37)

The information processing apparatus according to any one of (21) to (36), further including the plurality of arithmetic processing sections, in which the control section is configured to adaptively distribute the processing regarding instant output of medical data to the plurality of arithmetic processing sections.

(38)

The information processing apparatus according to any one of (21) to (36), further including the arithmetic processing section, in which the control section is configured to adaptively distribute the processing regarding instant output of medical data to the arithmetic processing section and an external arithmetic processing section.

(39)

The information processing apparatus according to (38), in which the control section is configured to acquire resource information including a usage fee of the external arithmetic processing section, and adaptively distribute the processing regarding instant output of medical data to the external arithmetic processing section on the basis of the resource information and a user's set budget.

(40)

The information processing apparatus according to any one of (21) to (39), in which each of the arithmetic processing sections includes at least a first arithmetic processing section including a field programmable gate array (FPGA), and a second arithmetic processing section including a graphics processing unit (GPU), the FPGA is switchable between at least two functions, and the control section is configured to switch the function of the FPGA on the basis of content of the processing and performance of the arithmetic processing sections.

(41)

The information processing apparatus according to any one of (21) to (40), further including a display control section configured to display a user interface indicating the arithmetic processing section allocated by the control section for each process executed as the processing regarding instant output of medical data.

(42)

The information processing apparatus according to (41), in which the display control section is configured to display an indication representing each of the arithmetic processing sections in the user interface by a display method corresponding to a type of the arithmetic processing section.

(43)

The information processing apparatus according to (42), in which the type of the arithmetic processing section includes whether or not the arithmetic processing section is an arithmetic processing section of the outside of the information processing apparatus.

(44)

The information processing apparatus according to (42) or (43), in which the display method includes at least one of a color, a density, a brightness, a size, a thickness, a line type, and a shape of the indication representing each of the arithmetic processing sections.

(45)

An information processing method, including adaptively distributing processing regarding instant output of medical data to a plurality of arithmetic processing sections.

(46)

An information processing system, including:

a control apparatus; and a plurality of arithmetic processing apparatuses, the control apparatus including a control section configured to adaptively distribute processing regarding instant output of medical data to an arithmetic processing section of each of the plurality of arithmetic processing apparatuses, the plurality of arithmetic processing apparatuses each including an arithmetic processing section configured to perform processing allocated by the control section.

REFERENCE SIGNS LIST

100 Endoscopic surgery system
101 Endoscope
139 CCU
201 Control section
202 Image processing section
211 GPU
212 FPGA
213 Combining processing section
251 Resource control section
261 Basic development section
262 Image-quality enhancement processing section
263 Detection section
264 Recognition section
265 Output data generation section
266 Resource information storage section
351 Resource control section
361 Combined data generation section
362 Output data generation section
401 Control device
501 Resource control section
511 Resource control section
601 Cloud computing

The invention claimed is:

1. A medical image processing apparatus for allocating at least two medical imaging processes to a plurality of assignable processing resources, the plurality of assignable processing resources being allocated by the medical image processing apparatus, the medical image processing apparatus comprising: circuitry configured to acquire medical image processing content, from medical equipment, to be processed according to the at least two medical imaging processes prior to display on a display device connected to a surgical operating room network, acquire a resource information of the plurality of assignable processing resources, allocate each of the at least two medical imaging processes to a different one of the plurality of assignable processing resources based on the resource information of the plurality processing resources and the medical image processing content, and allocate one of the at least two medical imaging processings to a graphics processing unit (GPU) during standard operations and allocate the one of the at least two medical imaging processings to a field programmable gate array (FPGA) during emergency operations.

2. The apparatus of claim 1, further comprising:
a first processor including the GPU and a second processor including the FPGA.

3. The apparatus of claim 1, wherein:
the circuity is configured to allocate to the FPGA a first of the at least two medical imaging processes with a parallel computational demand that is higher than a demand from a second of the at least two medical imaging processes.

4. The apparatus of claim 1, wherein
the circuitry is configured to allocate a region of interest (ROI) of a captured image to the GPU to perform image-quality enhancement on the ROI, and allocate a non-ROI portion of the captured image to the FPGA to perform basic image processing.

5. The apparatus of claim 1, wherein
the circuitry is further configured to display a visual indication on the captured image of a boundary between the ROI and the non-ROI portion of the captured image.

6. The apparatus of claim 5, wherein
the circuitry is configured to change an appearance of the visual indication to an indication of at least one of
an actuation of a diagnosis support function that supports identification of a lesion by machine learning, and
an expense incurred by employing an external processing resource.

7. The apparatus of claim 6, wherein
the change of appearance is displayed as at least a change of one of
color, line thickness, line type, blink duration, transmittance, or brightness.

8. The apparatus of claim 1, wherein
the resource information includes at least one of arithmetic performance, consumed power, response speed, availability of occupancy, cumulative operating time, hardware version, or usage fee.

9. The apparatus of claim 1, wherein
the circuitry is configured to change the allocation of the at least two medical imaging processes between the plurality of assignable processing resources based on the medical imaging processing content that includes a high temporal frequency region and a low temporal frequency region, the low temporal frequency region has a lower graphics processing demand than the high temporal frequency region.

10. The apparatus of claim 1, wherein
the at least two medical imaging processes include surgical assistance processing that includes at least one of
highlighting a lesion site on an image, and
displaying, as a superposition on the image, a cut part of the lesion site.

11. The apparatus of claim 1, further comprising:
a wearable computer that is configured to receive, detect, and process, as an input instruction, a user gesture, the wearable computer being at least one of a glasses-type wearable computer or a head mounted display.

12. The apparatus of claim 1, wherein the medical image processing content is acquired from a camera mounted on a multi-joint, multi-link surgical assistance support arm device that is driven by a plurality of actuators.

13. The apparatus of claim 1, wherein:
the circuitry comprises a first camera controller and a second camera controller, wherein
the first camera controller includes at least one of the plurality of assignable processing resources, and the second camera controller includes at least another of the plurality of assignable processing resources,
the first camera controller being configured to allocate a first of the at least two medical imaging processes to the at least one of the plurality of assignable processing resources included in the first camera controller, and allocate a second of the at least two medical imaging processes to the at least another of the plurality of assignable processing resources that is included in the second camera controller.

14. The apparatus of claim 1, wherein:
the circuitry comprises a controller, a first camera controller and a second camera controller, wherein
the first camera controller includes at least one of the plurality of assignable processing resources, and the second camera controller includes at least another of the plurality of assignable processing resources,
the controller includes circuitry configured to allocate a first of the at least two medical imaging processes to the at least one of the plurality of assignable processing resources included in the first camera controller, and allocate a second of the at least two medical imaging processes to the at least another of the plurality of assignable processing resources that is included in the second camera controller.

15. The apparatus of claim 1, wherein:
the circuitry comprises a camera controller that includes at least one of the plurality of assignable processing resources,
the circuitry being configured to allocate a first of the at least two medical imaging processes to the at least one of the plurality of assignable processing resources included in the camera controller, and allocate a second of the at least two medical imaging processes to the at least another of the plurality of assignable processing resources that is hosted external to the apparatus,
the at least another of the plurality of assignable processing resources is a cloud computing resource.

16. The apparatus of claim 15, wherein
the circuitry is further configured to display signal processing content confirmation information on a display, wherein indications of the at least two medical imaging processes are displayed in association with a first of the plurality of the assignable resources and a second of the plurality assignable resources so as to provide a visual indication of which of the at least two medical imaging processes are assigned to which of the plurality of the assignable resources.

17. The apparatus of claim 16, wherein
the circuitry is configured to display user-selectable control features that include at least one of
a frame size and/or shape of a region of interest (ROI),
a resource allocation indication,
a usage fee,
an occupancy allocation, and
an operation time of using a fee-for-use cloud processing resource.

18. A medical image processing method, executed in a medical image processing apparatus, for allocating at least two medical imaging processes to a plurality of assignable processing resources, the plurality of assignable processing resources being allocated by the medical image processing apparatus, the medical image processing method comprising: acquiring with the circuitry medical image processing content, from medical equipment, to be processed according to the at least two medical imaging processes prior to display on a display device connected to a surgical operating room network; and acquiring a resource information of the plurality of assignable processing resources; allocating with the circuitry each of the at least two medical imaging processes to a different one of the plurality of assignable processing resources based on the resource information of the plurality of assignable processing resources and the medical image processing content; and allocating one of the at least two medical imaging processings to a graphics processing unit (GPU) during standard operations and allocate the one of the at least two medical imaging processings to a field programmable. gate array (FPGA) during emergency operations.

19. A computing device comprising:
a display; and
circuitry configured to present on the display
first icons representing medical image processes to be performed on medical image content,
second icons representing at least one type of assignable processing resource, the second icons being displayed on the display in association with the first icons to indicate which of the assignable processing resources have been assigned to perform a particular one of the medical image processes, wherein allocation of the assignable processing resources are assignable from a menu of user-selectable resource information that lists the assignable processing resources that are available to be assigned to the medical image processes represented by the first icons, and change the allocation of the at least two medical imaging processes between the plurality of assignable processing resources based on the medical imaging processing content that includes a high temporal frequency region and a low temporal frequency region, the low temporal frequency region has a lower graphics processing demand than the high temporal frequency region.

* * * * *